United States Patent
Kadota et al.

(10) Patent No.: US 8,181,520 B2
(45) Date of Patent: May 22, 2012

(54) MUSCLE TRAINING DEVICE WITH MUSCULAR FORCE MEASUREMENT FUNCTION FOR CONTROLLING THE AXIAL TORQUE OF A JOINT AXLE

(75) Inventors: Kenji Kadota, Gunma (JP); Mamoru Tokita, Gunma (JP); Nobuharu Nishino, Gunma (JP)

(73) Assignee: Oki Electric Industry Co., Ltd., Tokyo (JP)

( * ) Notice: Subject to any disclaimer, the term of this patent is extended or adjusted under 35 U.S.C. 154(b) by 415 days.

(21) Appl. No.: 12/506,179

(22) Filed: Jul. 20, 2009

(65) Prior Publication Data

US 2010/0050765 A1     Mar. 4, 2010

(30) Foreign Application Priority Data

Aug. 29, 2008   (JP) ................... 2008-220613
Aug. 29, 2008   (JP) ................... 2008-220629
Sep. 16, 2008   (JP) ................... 2008-236696

(51) Int. Cl.
*A61B 5/22*     (2006.01)
*A63B 21/00*     (2006.01)

(52) U.S. Cl. ................ 73/379.01; 601/33
(58) Field of Classification Search ............ None
See application file for complete search history.

(56) References Cited

U.S. PATENT DOCUMENTS

| | | | |
|---|---|---|---|
| 6,992,456 B2 * | 1/2006 | Furuta et al. | 318/568.12 |
| 7,278,954 B2 * | 10/2007 | Kawai et al. | 482/1 |
| 7,857,774 B2 * | 12/2010 | Sankai | 601/5 |
| 7,904,203 B2 * | 3/2011 | Zaier | 700/245 |
| 7,998,096 B1 * | 8/2011 | Skoog | 601/5 |
| 2004/0097330 A1 * | 5/2004 | Edgerton et al. | 482/1 |
| 2007/0054777 A1 * | 3/2007 | Kawai et al. | 482/1 |
| 2008/0026923 A1 | 1/2008 | Kadota | |
| 2008/0161937 A1 * | 7/2008 | Sankai | 623/25 |

FOREIGN PATENT DOCUMENTS

| | | |
|---|---|---|
| JP | 2000-210272 A | 8/2000 |
| JP | 2007-061137 A | 3/2007 |
| JP | 2008-289507 A | 12/2008 |

OTHER PUBLICATIONS

T. Fujikawa et al., "Functional Coordination Control of Pairs of Antagonistic muscles", The Japan Society of Mechanical Engineers Technical Journal (C Edition), vol. 63, No. 607, pp. 769-776, Article No. 96-1040, referred to in paragraph 0003 of the description.

T. Fujikawa, et al., "Coordinating Functions among Antagonistic Pairs of Mono- and Bi-articular Muscles in Upper Extremity and Mechanical Model Analyses on Control Properties Induced by the Coordinating Muscular Functions", Bio-mechanism 13, The Society of Bio-Mechanisms Japan, pp. 181-193 (1996), referred to in paragraph 0033.

* cited by examiner

*Primary Examiner* — Lisa Caputo
*Assistant Examiner* — Jermaine Jenkins
(74) *Attorney, Agent, or Firm* — Rabin & Berdo, PC

(57) ABSTRACT

A training device measures, after its robot arm is mounted on a trainee, a change in angle of the joint axles of a limb of the trainee with angular sensors. Based on the angular change measured, a controller calculates an angular rate in the direction in which a load is applied, stores as the maximum muscular force a load at the time when the angular rate has exceeded a predetermined value, and stops applying the loads.

11 Claims, 24 Drawing Sheets

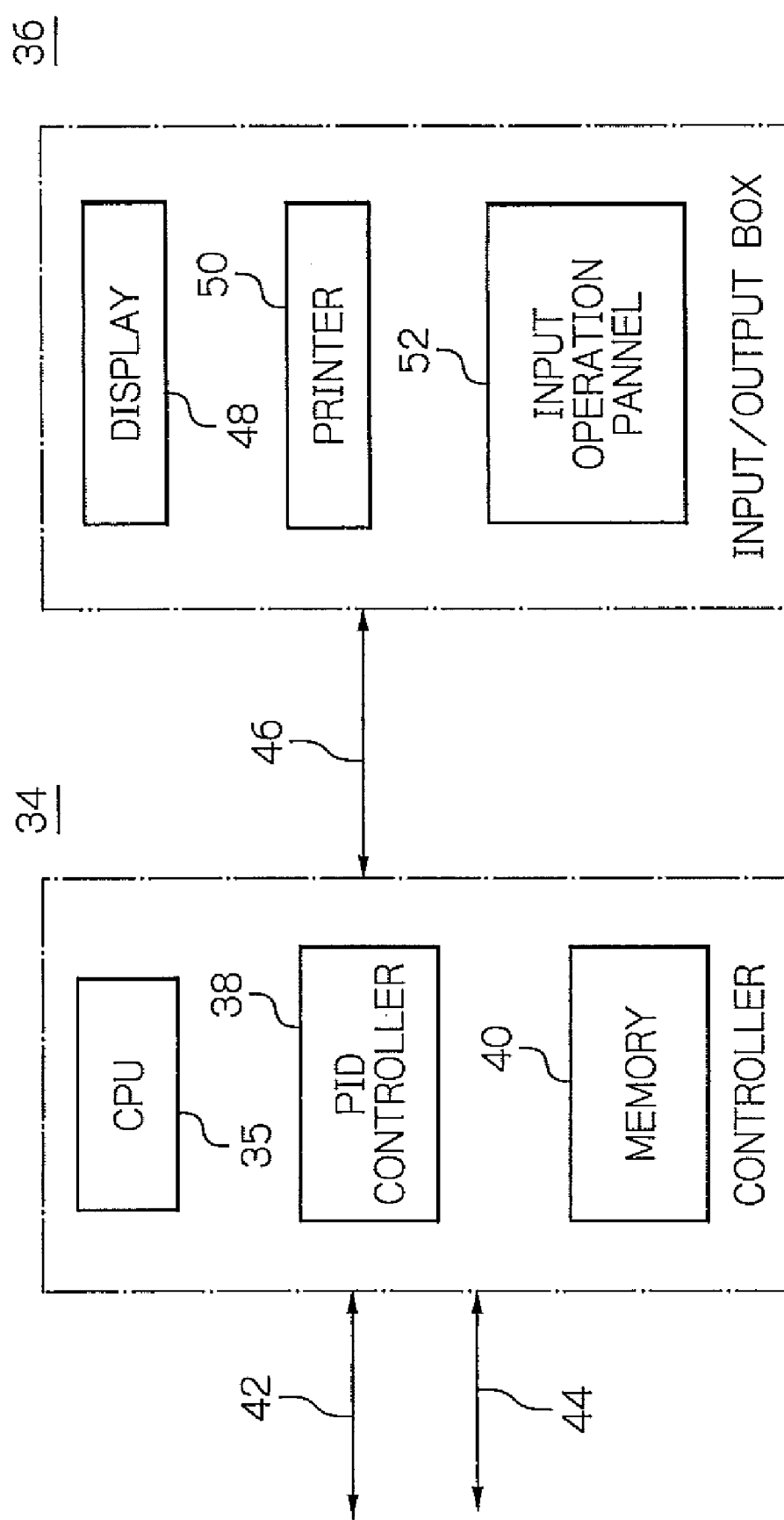

MUSCLE TRAINING DEVICE WITH MUSCULAR FORCE MEASUREMENT FUNCTION FOR CONTROLLING THE AXIAL TORQUE OF A JOINT AXLE

BACKGROUND OF THE INVENTION

1. Field of the Invention

The present invention relates to a muscle training device with muscular force measurement function.

2. Description of the Background Art

Conventionally, systems or devices have been proposed which exploit a bi-articular link mechanism, such as a bi-articular arm device, and for measuring and training muscular force. Such proposals are disclosed in Japanese patent laid-open publication Nos. 2000-210272 and 2007-61137 as well as in U.S. patent application publication No. US 2008/0026923 A1 to Kadota. In such systems and devices, outputs of the muscles in the antagonistic mono- and bi-articular muscle groups of a trainee are measured with a pressure sensor. Then, a limb of a trainee is caused to exert force in a plurality of predetermined directions with his or her isometrical maximum effort, on the basis of which a hexagonally shaped output distribution chart is formed to evaluate function-based muscles of praxis.

As an actuator for driving a bi-articular link mechanism, there has also been proposed a model of a bi-articular muscle functioning to flex the arms of the creature, including the human being, which has been used in a research of the motion control of the bi-articular link mechanism. Regarding such a proposal and research, there may be listed, as T. Fujikawa et al., "Functional Coordination Control of Pairs of Antagonistic muscles", The Japan Society of Mechanical Engineers Technical Journal (C Edition), Vol. 63, No. 607, pp. 769-776, Article No. 96-1040. In the research, in order to control rigidity and force at the distal end of an arm in the bi-articular link mechanism provided with a source of driving two joints simultaneously, it is said suitable to use a model of actuator comprising contraction and elastic elements exerting force in the contracting direction.

However, muscular force measuring and training devices in the prior art are so arranged that the members of a robot arm mounted on a limb of the trainee apply a load on the limb to measure and train the muscular force. As described above, when a load is actively applied to the trainee from a device mounted on the trainee, it is important to stop applying loads in a proper manner so as not to put the trainee in danger.

The measurement and training of muscular force cannot be attained unless the muscular force of the trainee is used to the limit. Consequently, for muscular force measurement and training devices it is significantly important to stop applying loads by appropriately determining the limit of the muscular force of the trainee. It is, however, difficult to correctly determine the limit of the muscular force of the trainee.

With muscular force training devices, training of muscles of praxis can be performed effectively, whereas the trainee grows easily tired because of the comparatively monotonic exercise. It is thus considered that practical exercise, such as bike riding, is employed so that the trainee can enjoy training.

For this, it has been proposed that a pseudo-bicycle type muscular force training device is used to change a load according to the angle of rotation to train specified muscles. However, since the muscular force training device of pseudo-bicycle type maintains for a comparatively short period of time a situation where a load is applied to the target muscle, compared with that in the entire exercise, it is difficult to achieve effective training.

Further, the muscular force measurement and training devices are so arranged that a load is applied to a limb of the trainee from the members of a robot arm mounted on the limb to perform measurement and training of the muscular force. Due to this, the sum of a load applied by the device, the own weight of the movable parts of the device and the own weight of the limb of the trainee become a load on his or her limb. Consequently, a load applied to the limb of the trainee cannot correctly be controlled unless the influence of the own weight of the movable parts of the device and the weight of his or her limb is taken into account.

SUMMARY OF THE INVENTION

It is an object of the present invention to provide a muscle training device with muscular force measurement function, ensuring safe measurement and training of muscular force without applying an excessive load on a trainee.

In accordance with the present invention, a training device with muscular force measurement function comprises a robot arm adjustable according to the length of either the upper limb or the lower limb of a trainee, a mounting fixture for mounting the robot arm on the trainee along either the upper limb or lower limb, an angular sensor for measuring the angle of rotation of the joint axle rotating integrally with the robot arm, while linking the robot arm correspondingly to the joint of the trainee, and a controller for controlling an axial torque of the joint axle, wherein the controller stores, when the angular rate of the joint axle in the direction of the axial torque exceeds a predetermined value, the value of the axial torque as the maximum muscular force of either the upper limb or the lower limb, and stops applying the axial torque when the angular rate exceeds the predetermined value.

Also in accordance with the present invention, a training device with muscular force measurement function comprises a robot arm adjustable according to the length of either the upper limb or the lower limb of a trainee, a mounting fixture for mounting the robot arm on the trainee along either the upper limb or the lower limb, an angular sensor for measuring the angle of rotation of the joint axle arranged in the robot arm, a torque sensor for measuring the axial torque of the joint axle, a controller for controlling the axial torque of the joint axle, and a memory for storing the axial torque of the joint axle and the angle of the joint axle, wherein the controller measures, before at least one of the muscular force measurement and the muscular force training is started, an axial torque supporting the own weight of the joint axle and generated by the own weight of either the upper limb or the lower limb and the own weight of the robot arm, and then stores the relationship between the measured axial torque supporting the own weight and the angle of the joint axle, based the stored relationship between the axial torque supporting the own weight and the angle of joint axle the axial torque of the joint axle is corrected in at least one of the muscular force measurement and the muscular force training.

Further in accordance with the present invention, a training device with muscular force measurement function comprises a robot arm adjustable according to the length of either the upper limb or the lower limb of a trainee, a mounting fixture for mounting the robot arm on the trainee along either the upper limb or the lower limb, an angular sensor for measuring the angle of rotation of the joint axle arranged in the robot arm, a torque sensor for measuring an axial torque of the joint axle, a controller for controlling the torque of the joint axle, and a memory for storing a reference table indicating the axial torque of the joint axle and the angle of the joint axle when the distal end of the robot arm moves to draw a predetermined orbit, wherein the controller generates an axial torque based on the relationship stored as the reference table in the memory, whereby the distal end of either the upper limb or the lower limb of the trainee is kept drawing the orbit and a training load on a specific group of function-based muscles of praxis is applied to either the upper limb or the lower limb of the trainee.

Still further in accordance with the present invention, a training device with muscular force measurement function comprises a robot arm adjustable according to the length of either the upper limb or the lower limb of a trainee, a mounting fixture for mounting the robot arm on the trainee along either the upper limb or the lower limb, an angular sensor for measuring the angle of rotation of the joint axle arranged in the robot arm, a torque sensor for measuring an axial torque of the joint axle, and a controller for controlling the torque of the joint axle, wherein the controller calculates, based on the relationship between an assumed virtual model and the actual posture of the robot arm, reactive force generated in the assumed model and applies a training load substantially equivalent to the reactive force to either the upper limb or the lower limb of the trainee.

In accordance with a training device with muscular force measurement function of the invention, a robot arm is mounted on a trainee with a mounting fixture to measure a change in angle of the joint axle of a limb of a trainee with an angular sensor. Based on the measured angular change, a controller calculates the angular rate in a direction in which a load has been applied to the joint axle to then store as the maximum muscular force a load at the time when the angular rate has exceeded a predetermined value, and stops applying the load. Thereby, the time when the muscles of the limb of the trainee exceed the peaks can be correctly determined, and thus the maximum muscular force of the trainee can correctly be measured, whereby a safe measurement and training of the muscular force can be performed without applying an excessive load to the trainee.

Further in accordance with a training device with muscular force measurement function of the invention, a robot arm is mounted on a trainee with a mounting fixture and a controller, before at least one of the muscular force measurement and the muscular force training is started, stores the relationship between the measured axial torque supporting the own weight and generated by the own weight of a limb of the trainee and the own weight of the robot arm and the angle of the joint axle. Based on the stored relationship, the controller corrects the axial torque associated with the implementation and drives the joint axle. Thereby, an intended load can be correctly applied to the limb of the trainee, and thus a safe measurement and training of muscular force can be performed without applying an excessive load to the trainee.

Further in accordance with a training device with muscular force measurement function of the invention, a robot arm is mounted on a trainee with an amounting fixture, and a controller generates an axial torque according to the angle of the joint axle obtained with an angular sensor for the robot arm mounted on the trainee along a limb of the trainee and applies a training load for a specific group of function-based muscles of praxis to the limb, while keeping the motional orbit of the trainee on a predetermined orbit. Thereby, training of the specific group of function-based muscles of praxis can effectively be performed, while the actual pattern of the motion is being reproduced, and thus the trainee can enjoy performing muscular force training for desired muscles safely and effectively.

Still further in accordance with a training device with muscular force measurement function of the invention, a robot arm is mounted on a trainee with a mounting fixture to measure with an angle sensor angle of the joint axle of the robot arm mounted on the trainee along a limb of the trainee to generate in a controller a torque according to the measured angle, and the controller calculates reactive force generated in a virtual model based on the relationship between an assumed virtual model and the actual posture of the robot arm to then apply a training load substantially equivalent to the reactive force to the limb of the trainee. Thereby, training of a specific group of function-based muscles of praxis can effectively be performed, while the pattern of the actual motion is being reproduced in a simulative fashion, and thus the trainee can enjoy muscular force training for desired muscles safely and effectively.

BRIEF DESCRIPTION OF THE DRAWINGS

The objects and features of the present invention will become more apparent from consideration of the following detailed description taken in conjunction with the accompanying drawings in which:

FIG. 2 is a block diagram schematically showing the configurations of a controller and an input/output box of the embodiment shown in FIG. 1A;

DESCRIPTION OF THE PREFERRED EMBODIMENTS

Figure 1A:
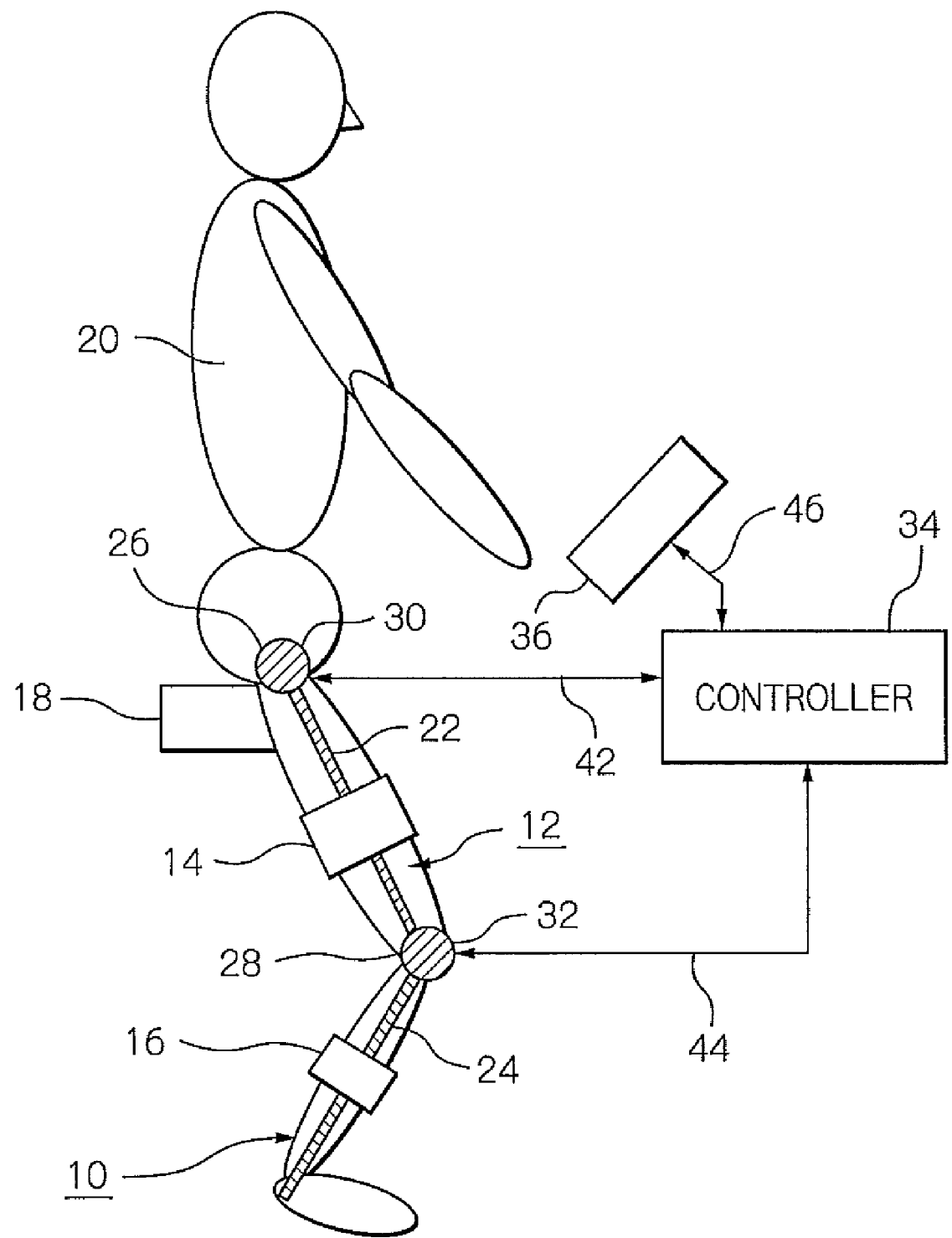
FIG. 1A is a side view and a partial block diagram of a preferred embodiment of a muscle training device, when mounted on a trainee, with muscular force measurement function in accordance with the invention.

In the following, with reference to the accompanying drawings, preferred embodiments of a training device with muscular force measurement function in accordance with the invention will be described in more details. Referring first to FIG. 1A, the embodiment of a training device with muscular force measurement function will be described in connection with the constitution and movement of the training device 10.

Figure 3:
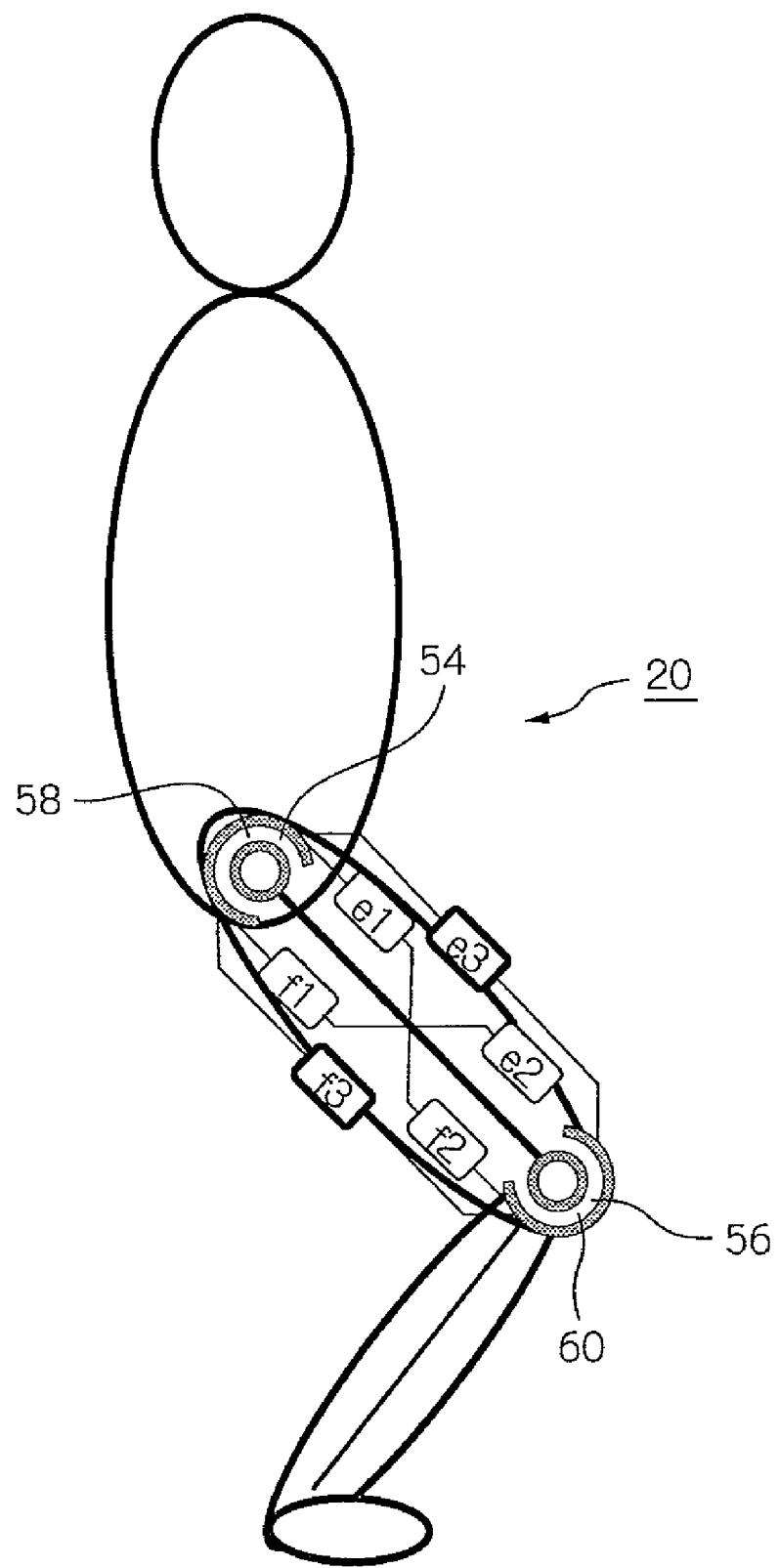
FIG. 3 schematically shows in a side view the relationship between the training device shown in FIG. 1A and a group of muscles of a limb of the trainee.

The training device 10 is so arranged that a robot arm 12 is mounted on a trainee 20 with mounting fixtures 14 and 16 to measure a change in angle of the joint axles 30 and 32 of a limb of the trainee 20 with an angular sensor 54 or 56, FIG. 3, and based on the measured angular change a controller 34 calculates an angular rate of the joint axles 30 and 32 in a direction in which a load has been applied to then store as the maximum muscular force a load at the time when the angular rate has exceeded a predetermined value and stops applying the load. Thereby, the time when muscular force of the limb of the trainee 20 exceeds its peaks can be determined correctly as well as the maximum muscular force of the trainee 20 can be correctly measured, and thus, measurement and training of muscular force can be performed safely without applying an excessive load on the trainee 20. Parts not directly related to understanding the invention are omitted from the figures and description.

Figure 1B:
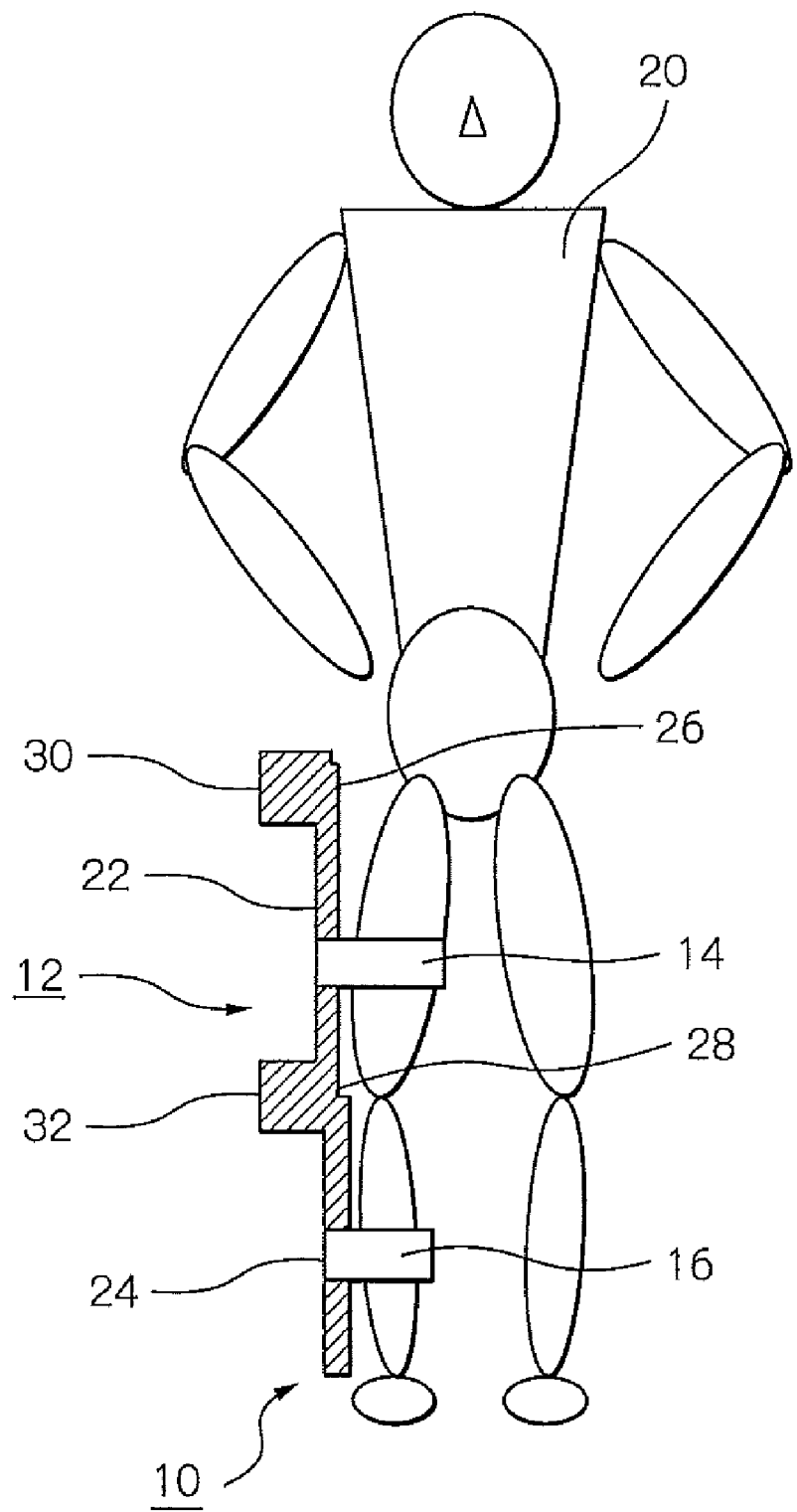
FIG. 1B is a front view of the illustrative embodiment shown in FIG. 1A.

With reference to the side and front views of FIGS. 1A and 1B, the illustrative embodiment of training device 10 with muscular force measurement function includes a robot arm 12 denoted by hatching and mounting fixtures 14 and 16. The training device 10 is adapted not only to measure function-based muscle forces of praxis based on the theory of coordinately controlling function-based muscles of praxis in which the output of the distal ends of a limb is controlled coordinately by mono- and bi-articular muscles present in the limb, taking output characteristics of the human limb into account, but also to practice effective training. The training device 10, in particular, is directed to a case of being mounted on the trainee, i.e. user, 20 along his or her limb in posture sitting on a saddle. The training device 10 is not exclusively applicable to the case when mounted on a lower limb, but to a case when mounted on an upper limb of a trainee.

A system disclosed in the Japanese '272 publication indicated earlier requires a user to exert force in a plurality of directions with his or her maximum effort, because a hexagonally shaped output distribution chart is required to be formed for the distal end outputs of a limb to be measured for function-based muscles of praxis.

Further, since that conventional system measures the distal end output with a fixed sensor on which the user exerts his or her force, it is required to guide the force in a direction to be measured. As a method for guiding the direction of the force, there may be considered a visually indication and the biofeedback as disclosed by Kadota stated earlier.

However, either method requires the habituation of the user, who is required to have skill in controlling his or her force while exerting it with the maximum muscular force. Also, since force cannot necessarily be exerted in a direction to be measured, measurement has to be made over again in some cases. Accordingly, those methods will result in the user being forced to bear an inordinate burden. It is the training device with muscular force measurement function 10 that solves the above problems involved in the system disclosed in the Japanese '272 publication.

The robot arm 12 of the illustrative embodiment includes links 22 and 24, joint axles 26 and 28, and servo motors 30 and 32. The robot arm 12 also includes a controller 34 and an input/output box 36.

The two links 22 and 24 are arms having two degrees of freedom. The link 22 is a supporting member for arranging the joint axles 26 and 28 as well as a slide mechanism, not shown, corresponding to the thigh, while the link 24 is another supporting member for arranging the joint axle 28 and a slide mechanism corresponding to the lower thigh.

The slide mechanism has the function for adjusting the length of the link. The slide mechanism, at the time of evaluation and training of muscular force, adjusts the lengths of the links to be approximately equal to those of the upper and lower thighs of the user 20, respectively. The slide mechanism may employ a nested structure as shown in Japanese patent laid-open publication No. 2008-289507 to make the link on the side of the second joint slidable in its longitudinal direction against the link on the side of the first joint, not shown, to thereby contract the link 22. By means of this method, the link 22 is adjusted for its length to be approximately equal to the thigh of the user 20. The joint axles 26 and 28 will be described later in detail.

The joint axles 26 and 28 have the function to rotate correspondingly to joints applied to a desired limb in evaluation and training of muscular force. The servomotors 30 and 32 have the function to generate loads on a desired limb in evaluation and training of muscular force. In this way, the servomotors 30 and 32 function as sources for driving the joints to generate torques for rotating the joint axles. The torque is controlled with a controller 34.

The controller 34 has the function to control the axial torque of the source for driving joints as well as to control displaying and recording. The controller 34, as shown in FIG. 2, includes a CPU (Central Processing Unit) 35, a PID (Proportional Integral Differential) controller 38 and a memory 40. The CPU 35 has the function to arithmetically operate the algorism of the training device 10 with muscular force measurement function. The PID controller 38 has the function to control the voltage of driving the servomotors 30 and 32 based on angular sensor data obtained from a torque sensor and an angular sensor, which will be described later, arranged in the servomotors 30 and 32. Accordingly, the controller 34 feeds driving signals 42 and 44 to the servomotors 30 and 32. The controller 34 controls the axial torque of the joint driving source in response to the driving signals. The memory 40 has the function to store muscle evaluation data and torques of the user 20 in the form of reference table. The device having such a storing or recoding function is not limited to the specific type of memory 40, which may be implemented as a hard disc device, for example. In the description, signals will be indicated with reference numerals for respective connecting wires they appear.

The controller 34 is connected to the input/output box 36 to deal with data 46. The input/output box 36, as shown in FIG. 2, includes a display 48, a printer 50 and an input operation panel 52. The display 48 may be a CRT (Cathode-Ray Tube) or a liquid crystal display (LCD) which is adapted to visually display the muscular force evaluation data. The printer 50 is adapted to visualize on a thermo-sensitive paper a torque generated by the joint axles of the robot arm 12. Also, the printer 50 prints the magnitude and direction of the torque and force exerted by the robot arm 12, or it prints the direction of force to be exerted to the user 20 and the amount of change in his or her posture. The input operation panel 52 has the function to enter set data or instruction data representing the user's intention to perform muscular force evaluation.

Going back to FIG. 1A, the mounting fixtures 14 and 16 have the function to fasten the two links 22 and 24, respectively, to a limb desired for muscular force evaluation and training. The mounting fixtures 14 and 16 fasten the links 22 and 24 to the upper and lower thighs, respectively, in the embodiment.

The general interconnections between those components will be described in brief. The robot arm 12 is mounted on the user while sitting on a saddle 18. Now, the robot arm 12 is coincided by the joint axle 26 with the hip joint axle of the user 20 and by the joint axle 28 with the knee joint axle of the user 20. Also, to the joint axles 26 and 28 there are connected the servomotors 30 and 32. Further, the joint axles are provided with absolute type encoders or rotary encoders 54 and 56 as angular sensors for measuring the angles of the joint axles. Correspondingly, the joint axles 26 and 28 have torque sensors 58 and 60, FIG. 3, arranged on the rotary shafts thereof for measuring torques.

Figure 4:
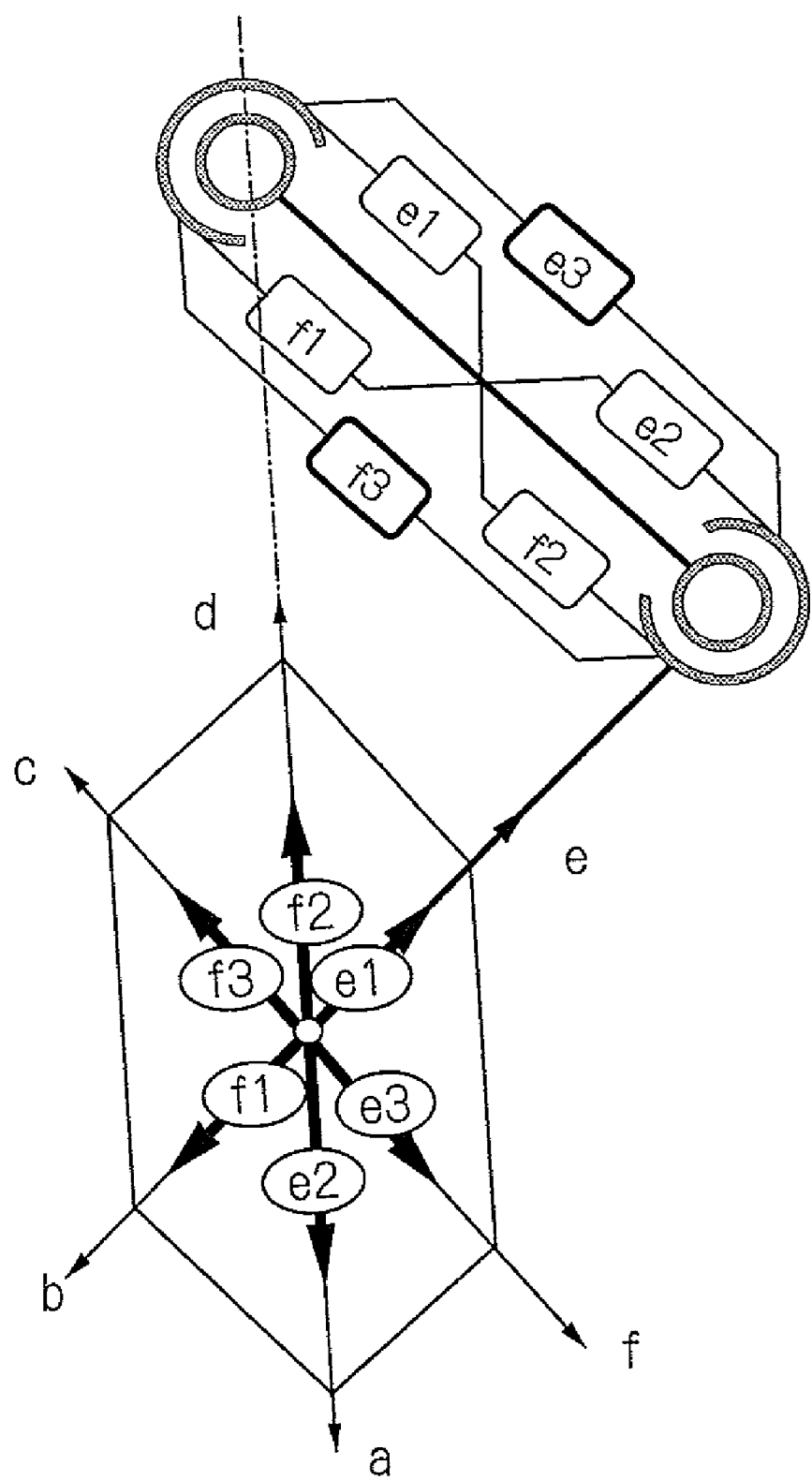
FIG. 4 shows output distribution characteristics in the limb of the trainee shown in FIG. 3.

Subsequently, a group of muscles of a user 20 in the embodiment is schematically shown in FIG. 3. To begin with, description will be made for a bi-articular joint link mechanism of the human muscles constituting the background of the training device 10. There exist bi-articular muscles in the limbs of the human being. The bi-articular muscle controls an output from the distal end thereof in coordinate with a mono-articular muscle acting on a single joint. The distal end output has been known as being represented with hexagonally shaped output distribution as shown in FIG. 4. The output distribution is disclosed in T. Fujikawa, et al., "Coordinating Functions among Antagonistic Pairs of Mono- and Bi-articular Muscles in Upper Extremity and Mechanical Model Analyses on Control Properties Induced by the Coordinating Muscular Functions", Bio-mechanism 13, The Society of Bio-Mechanisms Japan, pp. 181 (1996). A method for evaluating function-based muscles of praxis on the basis of hexagonally shaped output distribution has been known in the earlier mentioned T. Fujikawa, et al.

Subsequently, description will be made for the distal end output characteristics of a limb disclosed in T. Fujikawa et al., stated just above and in the Japanese '272 publication. In respect of movement on a two-dimensional plane, the upper and lower limbs of the human being, including the first and the second joint axle and the distal end of the system, if the functions of the muscles are taken into account, a group of muscles acting on the first and second joint axles may be represented by three paired muscles, totaling at six muscles, constituted of an antagonistic mono-articular muscle pair (f1, e1) around the first joint axle, an antagonistic mono-articular muscle pair (f3, e3) around the second joint axle and an antagonistic mono-articular muscle pair (f3, e3) laying astride the first and second joints. The three paired muscles are termed function-based muscles of praxis. The example shown in FIG. 3 is a group of muscles acting on the hip and knee joints of the lower limb of the user 20.

The mono-articular muscle is a muscle acting only on a single joint. In respect of the upper limb, it corresponds to the anterior and posterior regions of the deltoid muscle of the shoulder joint, and the muscle of the upper arm linked to the cubital joint and the lateral head of the tricepts thereof. In respect of the lower limb, it corresponds to the musculus gluteus maximus and the major psoas muscle linked to the hip joint, and the short head of bicepts femoris muscle linked to the knee joint and lateral vastus muscle thereof.

The bi-articular muscle is a muscle acting astride two joints. In respect to the upper limb, it corresponds to the bicepts brachii muscle of the upper muscle and the long head of tricepts brachii muscle thereof. In respect to the lower limb it corresponds to hamstrings and the rectus femoris muscle.

Figure 5:
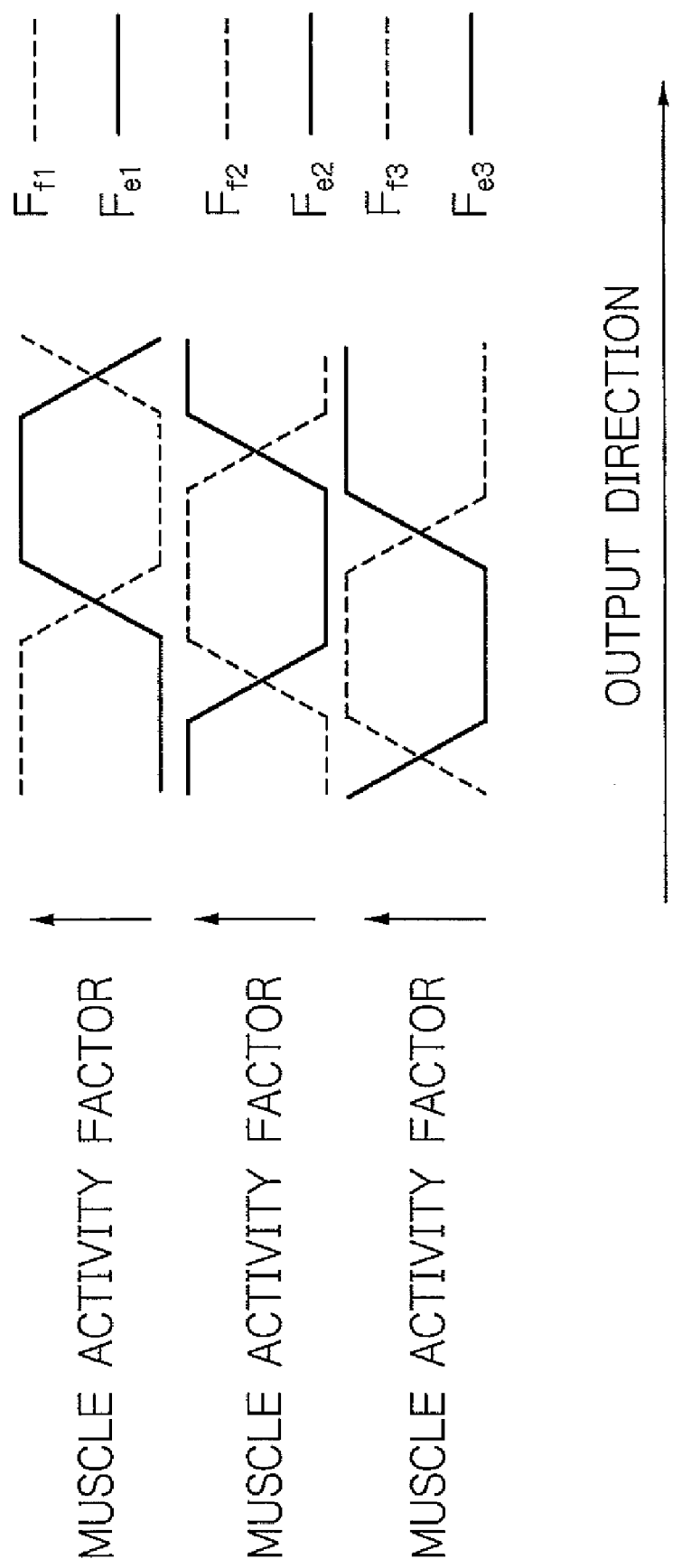
FIG. 5 shows activity patterns of the muscles in the limb of the trainee shown in FIG. 4.

The output and the direction of output exerted in the distal end of the bi-articular link system of the upper and lower limbs of the human being, i.e. the wrist joint region in the upper limb and the ankle joint in the lower limb, are controlled with coordinating activities of the function-based muscles of praxis having three paired muscles, totaling at six muscles. When force is exerted with the maximum effort at this distal end, the function-based muscles of praxis having three paired muscles, totaling at six muscles, alternately contract according to the output direction of the force, as shown in FIG. 4. Force F representing muscular activities in FIG. 5 represents the force of the joint muscle denoted with subscripts.

The directions of the force generated at the distal ends of a human limb due to the contracting force exerted by the function-based muscles of praxis of three paired muscles, totaling at six muscles, are as shown in FIG. 4. Further, composition of the forces resulting from the coordinating control according to the alternative pattern is represented with hexagonally shaped maximum output distribution characteristics, as shown in FIG. 5.

The sides of the hexagon of the maximum output distribution characteristics are characterized by being in parallel with the links 22 and 24, and the straight lines connecting the first joint and the distal end of the system. Accordingly, the shape of the hexagon varies depending on the posture of a human limb. Even when a torque generated in each joint does not vary in the state of the contracting force of the muscles being at a constant level, the force generated at the distal end of a human limb changes not only in direction but also in magnitude due to the joint torque, depending on the posture of the upper or lower limb.

Subsequently, operation of the training device 10 will be described. To begin with, description will be made for basic operation to perform measurement and training of muscular force. The distal end of the link system corresponds to the wrist joint in the upper limb and to the ankle joint in the lower limb. The output distribution of the force at the distal end of the link system is shown in FIG. 5A and the output distribution of the torque of the joint axle in FIG. 6B.

The output distribution of the force exerted at the distal end of the link system varies depending on an articular angle of the link system. Thus, in the embodiment, as shown in FIG. 6B, the abscissa axis represents the first joint axle torque ($\tau_1$) and the ordinate axis represents the second joint axle torque ($\tau_2$). A distribution chart of the joint axle torques will be examined in which the torques simultaneously generated in the first and second joint axles are plotted.

Figure 6A:
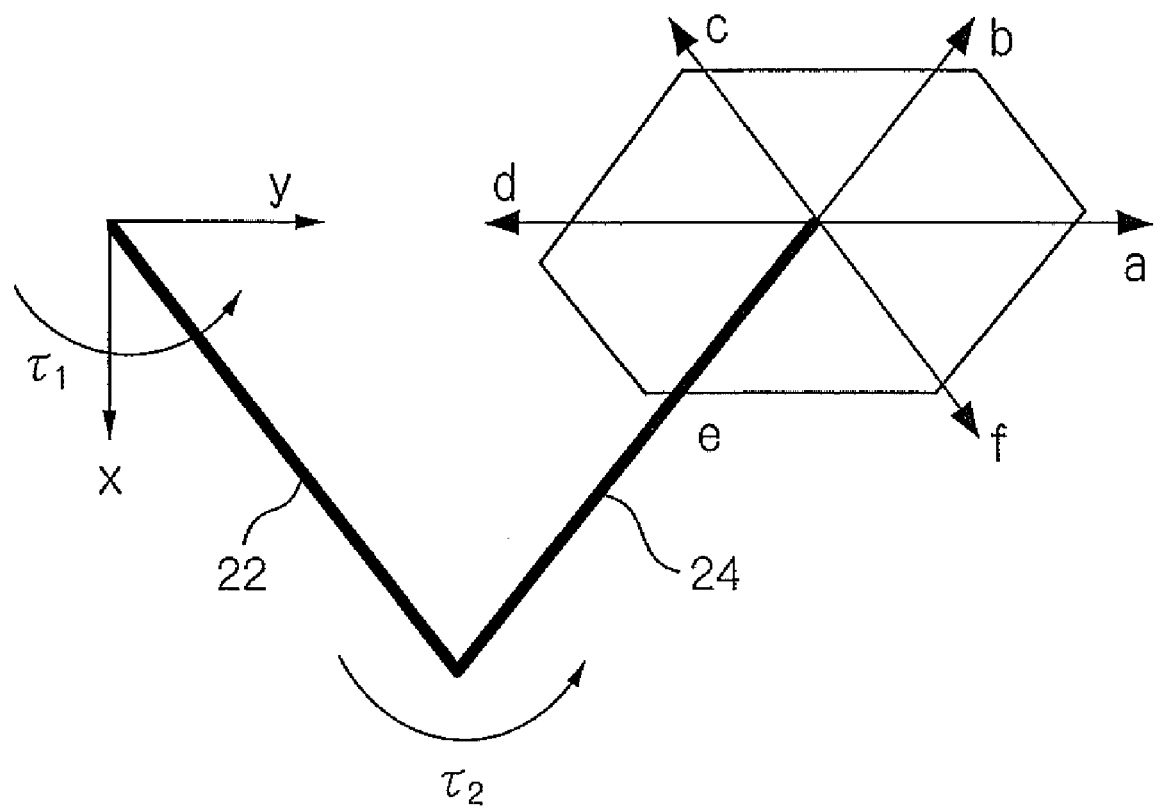
FIG. 6A shows output distribution characteristics of the distal end of a link system in the training device shown in FIG. 1A.
Figure 6B:
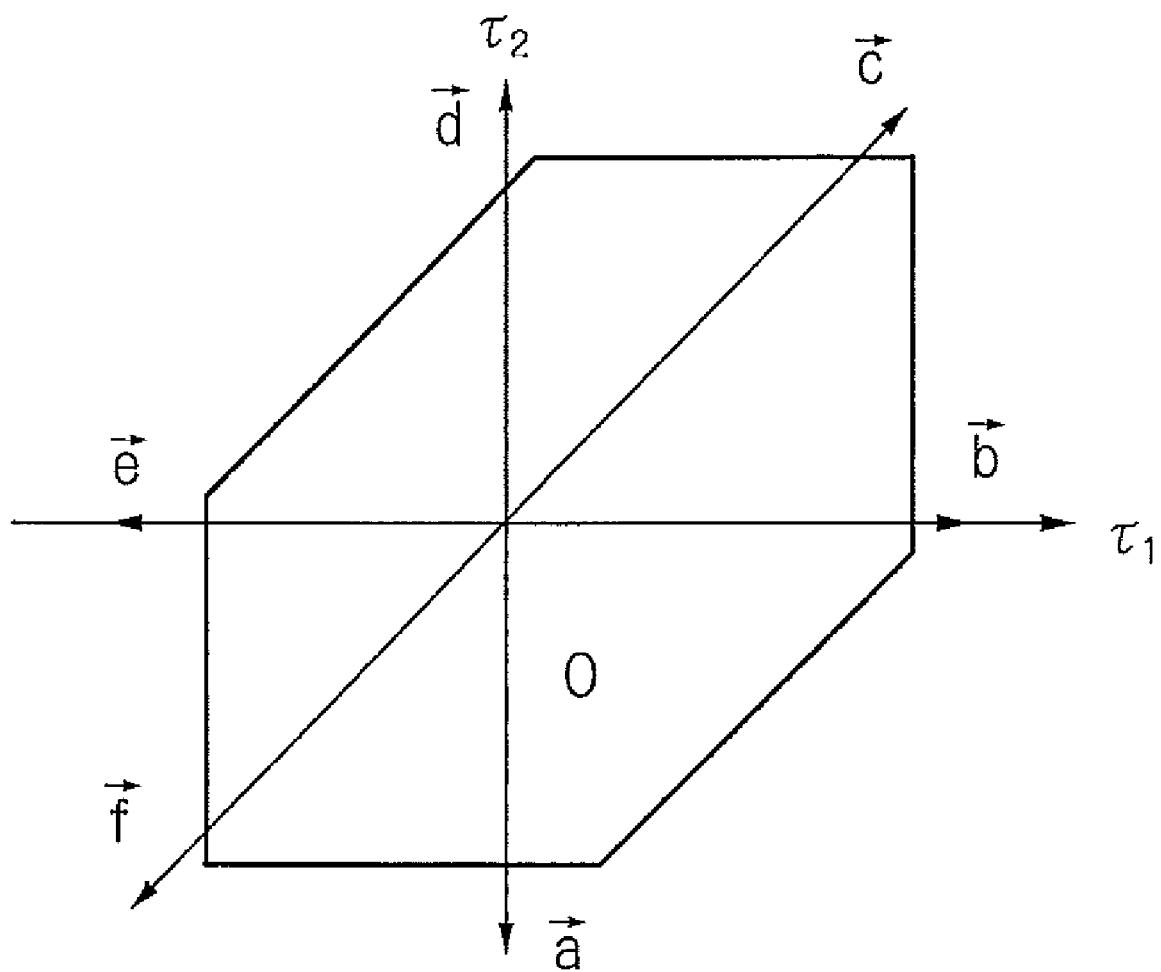
FIG. 6B shows output distribution characteristics of torques of the joint axle in the training device shown in FIG. 1A.

According to the theory of function-based muscles of praxis, an output distribution chart of the joint axle torque is hexagonal, as shown in FIG. 6A, like the output distribution chart of the distal end of the link system. In FIGS. 6A and 6B, the output distribution charts of the joint axle torque and the distal end of the link system are shown in a fashion corresponding to each other.

The output distribution chart in FIG. 6A corresponds to the output distribution characteristics of the Japanese '272 publication. In this hexagon, the second lever, i.e. two sides in parallel with the link 24, does not change in its moment against the second joint. Accordingly, in the output distribution chart, $\tau_2$=constant, i.e. $\tau_2$ is equivalent to a straight line in parallel with $\tau_1$ axis. Correspondingly, in the hexagon of FIG. 6A, two sides in parallel with a straight line connecting the first joint and the distal end of the link system do not change in their moment for the first joint. Accordingly, in the output distribution chart of the joint axle torque, $\tau_1$=constant, i.e. $\tau_1$ is equivalent to a straight line in parallel with $\tau_2$ axis.

With regard to the first lever, corresponding to two of the sides of the hexagon shown in FIG. 6A which are in parallel with the link 22, when change in force applied from either one apex to the other apex of the two sides is taken into account, it is considered that the direction is coincide with the direction of the link 22 and the first and second joints are subject to substantially equal change in torque. Therefore, the first lever is equivalent to a straight line in parallel with a straight line of $\tau_1=\tau_2$. If an output distribution chart of axial torque like one shown in FIG. 6B can be measured, it is also possible to obtain an output distribution chart of the distal end of the link at an optional joint angle. To evaluate individual muscle force of the function-based muscles of praxis, a lean muscle section area of a pair of antagonistic bi-articular muscles may be specified for estimation, as discussed in the Japanese '272 publication.

To obtain an output distribution chart of joint axle torques in the training device 10, forces exerted in different directions by the user 20 with his or her maximum effort in the state of the robot arm 12 being mounted on the user 20 along his or her lower limb is recorded as joint axle torques. In such a case, the user 20 is caused to exert his or her force, while being indicated with a direction of the force on some means for displaying it. Further, since reactive force is generated against the user by controlling the joint axle torque in a way that the joint angle does not change, the robot arm 12 records as a joint axle torque generated by the user 20 the joint axle torque at the time when the joint angle does not change.

Figure 7:
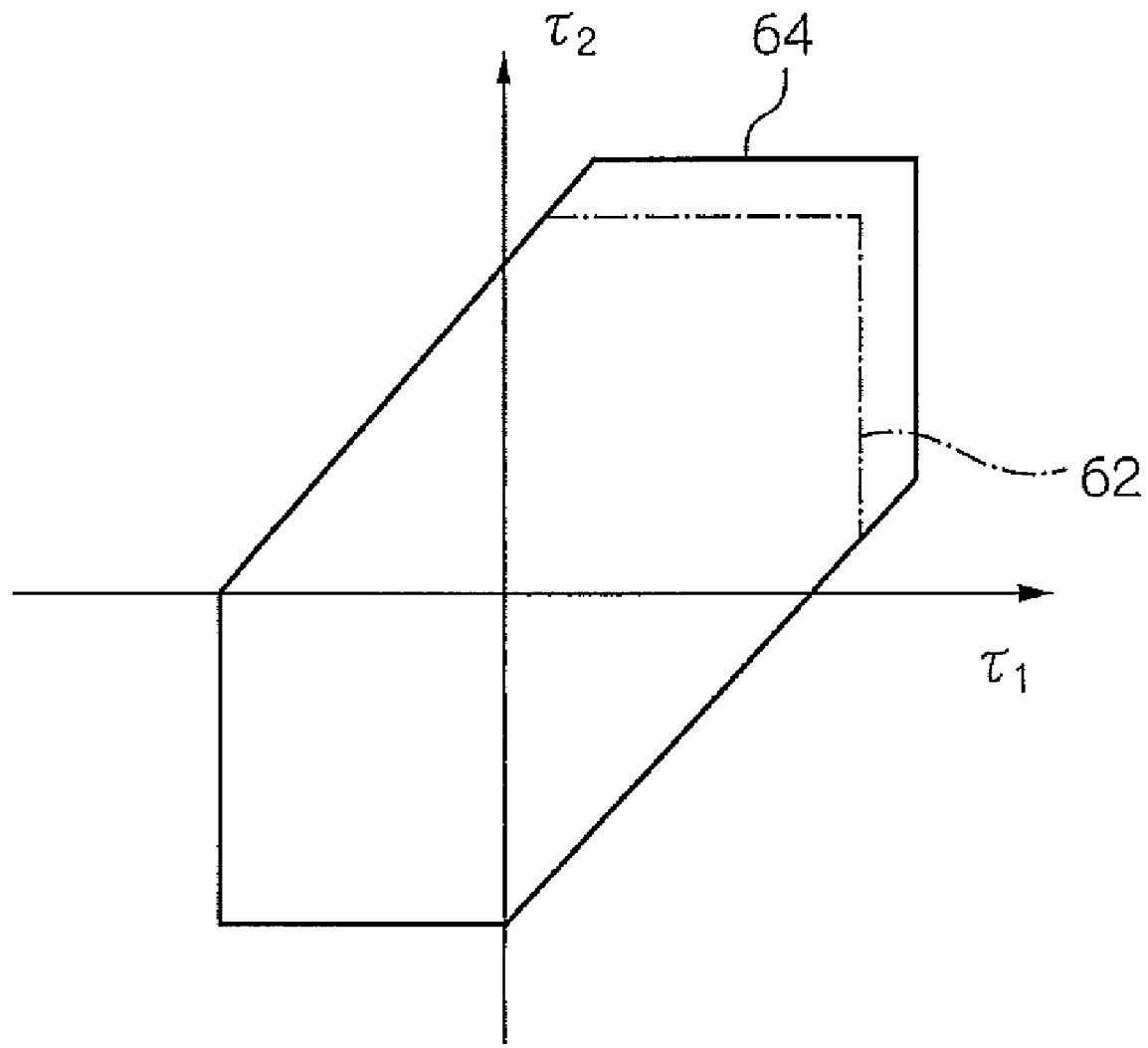
FIG. 7 shows change in output distribution of torques of the joint axle before and after training in the training device shown in FIG. 1A.

Subsequently, change in an output distribution chart of joint axle torques before and after the training in the embodiment is shown in FIG. 7. The recorded joint axle torques are plotted on a $\tau_1$-$\tau_2$ coordinate plane shown in FIG. 7 as torques simultaneously generated by two joint axles. The plotted joint axle torques are included as an aggregate of plots inside a hexagon, which is an output distribution chart of joint torques. In other words, the hexagon is drawn as the smallest hexagon with two sides being in parallel with $\tau_1$ axis, with other two sides being in parallel with $\tau_2$ axis and with the remaining two sides being in parallel with a straight line of $\tau_2=\tau_1$.

Hexagons 62 and 64 which the user 20 uses the training device 10 to draw on the display before and after his or her training performed, respectively, are indicated on the $\tau_1$-$\tau_2$ coordinate plane of the same screen, thereby making it possible to grasp change in muscle before and after the training.

In the training, it is possible to use the training device 10 as well. When training, the user 20 first manipulates the input operation device 36 of the training device 10 to enter a training menu. The entry of the training menu includes the output direction desired to be increased at the distal ends of his or her own body limb and the magnitude of the training load on the basis of a hexagon of the maximum output distribution characteristics, for example as shown in FIG. 4.

For example, in case of intending to extend a skip distance in standing broad jump, when the user 20 desires to increase an output of the distal end in the direction b in a hexagon like one shown in FIG. 4, he or she selects the direction b as an output direction of his or her training and enters the magnitude of the training load. Then, in the case that force is exerted in the direction b from an alternative pattern of three-paired six muscles of praxis like one shown in FIG. 4, it is clearly seen that the activating muscles are a group of mono-articular flexors of hip joint f1, a group of mono-articular flexors of knee joint e2 and a group of bi-articular flexors of thigh f3.

To increase the output of the distal end in the direction b, a group of mono-articular flexors of hip joint f1, a group of mono-articular flexors of knee joint e2 and a group of bi-articular flexors of thigh f3 may be trained, and therefore, the training device 10, when those three muscle groups are activated, increases in the opposite direction torques generated by the servomotors 30 and 32 corresponding to the hip and knee joints gradually, or in a stepwise fashion up to the magnitude of the training load entered by the user 20. Then, the user 20 exerts his or her force in antagonism to the torque generated by the training device 10, whereby he or she can maintain the state of generating a predetermined muscular output for training of muscular force.

Since the training device 10 applies a predetermined torque as a load on the user 20, the user 20 can perform isometric training by making an effort not to change the position of distal ends of his or her body, i.e. the ankle region in the embodiment. Further, even when the user 20 has changed his or her posture during training, a load on the muscle does not change. Consequently, it is possible to perform isometric training as well.

As described above, when the user 20 intends to evaluate the muscles changed by training of some kind, i.e. to evaluate difference in the changed muscles, he or she can evaluate from the change in a hexagon showing the output distribution of joint axle torques what type of change has been obtained, even though individual muscular force of the function-based muscles of praxis is not necessarily be specified. For example, if some kind of training has caused the output distribution chart of joint axle torque to change as shown in FIG. 7, it is possible to evaluate that an effect has been obtained which is equivalent to that in case of the muscular force of the function-based muscles being increased.

The training device 10 is so arranged that it applies a load on the user 20 and causes the user 20 to exert an output antagonistic to the load in such a way that the user 20 does not move from his or her position in antagonism to the load. When the training device 10 gradually increases the magnitude of force in a specified direction, the load reaches the maximum muscular force at the instance when the user 20 gives in to the load generated by the training device 10. As the force generated by the training device 10 is controllable for its direction and magnitude, the user 20 can measure his or her maximum output in a specified direction by simply exerting force not to move from his or her position.

When a load is applied on the user 20 from the training device 10, it is important for the training device 10 to determine the maximum muscular force of the user 20 accurately and then stop applying the loads. When the muscular force of the user 20 has exceeded the limit, an excessive load would be applied on the user 20, which is thus undesirable. By contrast, when application of a load is stopped before the limit of the muscular force, the maximum muscular force could not be measured. At this instance, the user 20 would terminate the exercise without having actual feeling of using every exertion of his or her force.

Here, as a measure for determining the maximum muscular force of the user 20, there could be considered a method for determining as the maximum muscular force a load at the time when the distal end positions of a limb or the joint angles vary to exceed a predetermined level, compared with that at the start measuring.

In the illustrative embodiment, however, an angular change of the joint axles of a limb of the user 20 is measured to determine as the maximum muscular force a load at the time when the angular rate of the joint axles in a direction in which the load has been applied has exceeded a predetermined value. Thereby, the training device 10 can more accurately measure the maximum muscular force.

In more specific, the training device 10 measures the angles of the joint axles 26 and 28 of the robot arm 12 and records as the maximum muscular force of the upper or lower limb of the user 20 a torque value at the instance when the angles of the joint axles 26 and 28 in a direction in which a load applied by the servomotors 30 and 32 exceeds a predetermined value, and in turn the device 10 will stop applying torques.

Subsequently, it will be described in detail with reference to FIG. 8 how to determine the maximum muscular force in the embodiment. To begin with, the user 20 gradually changes his or her posture in antagonism to force generated by the robot arm 12 fastened to his or her lower or upper limb. As for change in posture of the user 20 there are considered three factors. They are firstly a factor that the user 20 tends to exert force larger than the force generated by the robot arm 12, secondly a factor that the user 20 tends to exert force in a direction different from the direction of the force generated by the robot arm 12 after looking for a direction in which his or her force is to be exerted, and thirdly a factor that the user 20 tends not to be instantaneously antagonistic sufficiently to the force generated by the robot arm 12.

The change in posture attributable to the first and second factors occurs in the user 20. With reference to FIG. 8, the change in posture occurs between a no-loaded range of torque 68 denoted with an arrow 66 where application of the load is unconditionally stopped and a blind sector range denoted with an arrow 70. The range indicated with the arrow 70 represents a period of time during which force generated by the robot arm 12 in an initial stage where the user starts exerting his or her force is small and during which the change in posture occurs in a direction opposite to the direction of applying the load, which is indicated with an arrow 72. Then, the training device 10 starts measurement after the user 20 has reached a predetermined angle 74 of the joint axle. The range indicated with an arrow 76 is also a blind sector range of the user 20.

Further, a change in posture of the user 20 attributable to the third factor occurs in a state where force generated by the robot arm 12 increases to be close to the maximum muscular force of the user 20 in the range between the joint axle angles 80 and 82 indicated with an arrow 78. Moreover, when the measured joint axle angle increases to exceed the joint axle threshold angle 82, application of the load is unconditionally stopped.

Accordingly, when an erroneous determination of the maximum muscular force is made for change in posture of the user 20 attributable to the third factor, not only measurement of the maximum muscular force cannot be made but also some time has to be spared for the restart of the measurement until the measurement is started again, because of the fatigue of the user 20. Further, as for the change in posture of the user 20 attributable to the third factor, if the user 20 can retain again his or her posture after changing the posture, it can be considered that the user 20 has muscular force substantially equivalent to the force being generated by the robot arm 12. Consequently, to determine the maximum muscular force only on the basis of the change in posture would possibly be unable to accurately measure the maximum muscular force.

Figure 8:
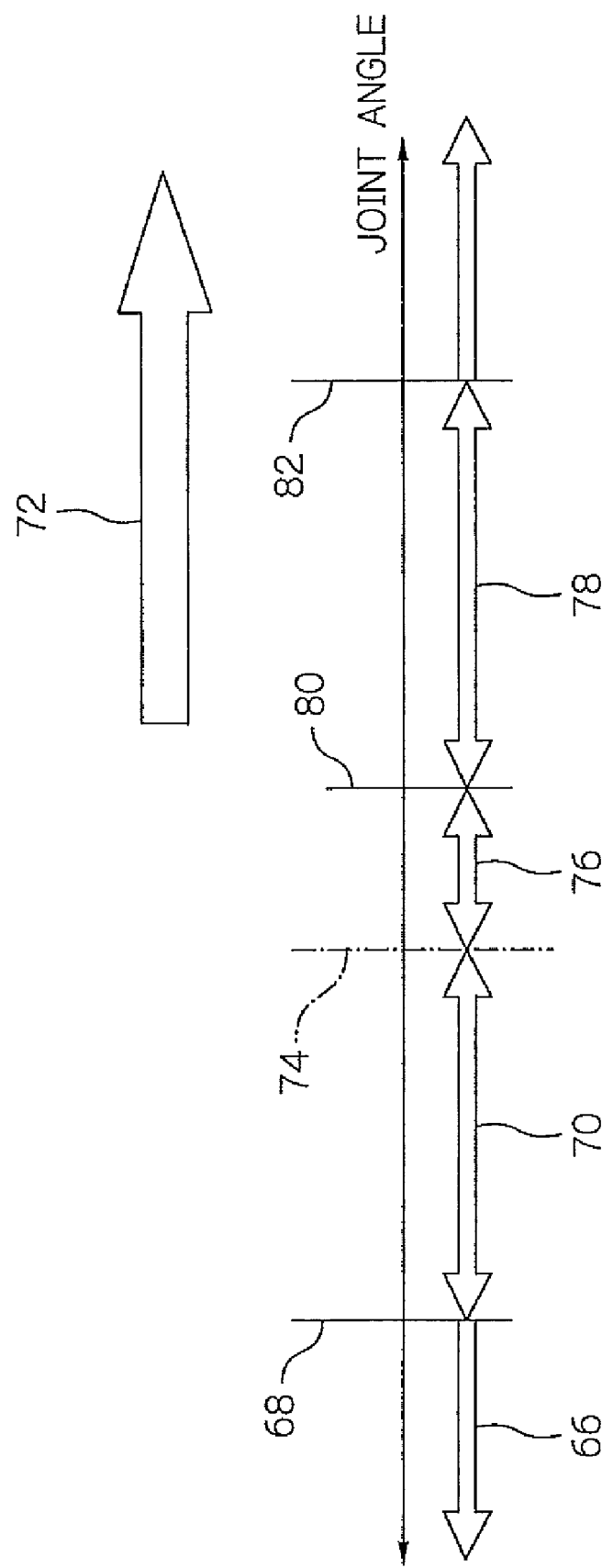
FIG. 8 shows how to determine the maximum muscular force in the training device shown in FIG. 1A.

Thus, the training device 10 in accordance with the illustrative embodiment, as shown in FIG. 8, sets a broader allowable range in variation of the joint axle angle of the upper or lower limb of the user 20 within a range where the safety of the user 20 can be secured, and then, it measures the maximum muscular force based on a joint angular rate, which is an angular rate of the joint axle.

Since the human being cannot keep on exerting the maximum muscular force, force exerted by the user 20 gradually decreases from a certain point and a speed at which the user 20 is pressed by the robot arm 12 increases. Due to this, by monitoring the angular rate of the joint axle, more accurate measurement of the maximum muscular force of the user 20 can be performed.

In addition, the angular rate of the joint axle of the user 20 is measured as an amount of change in angle at a certain time interval of about 1 to 5 [ms] by angular sensors of absolute type or rotary encoders provided in the joint axles 26 and 28 of the robot arm 12. When during measurement of muscular force shown in FIG. 8 a joint angular rate exceeding a predetermined value is measured in the direction 72 of a torque generated by the robot arm 12 in its joint axles 26 and 28, the output of the robot arm 12 at that instance is regarded as the user 20 having reached the maximum muscular force and the operation of the robot arm 12 is stopped.

The training device 10 thus measures a change in angle of the joint axles 26 and 28 of a limb of the user 20, and determines as the maximum muscular force a load at the instance when angular rates of the joint axles 26 and 28 in a direction in which loads are applied exceed a predetermined value, thereafter stopping the operation of the robot arm 12. In other words, the controller 34 of the training device 10 measures angles of the joint axles 26 and 28 of the robot arm 12 and records as the maximum muscular force of the upper or lower limb of the user 20 a torque value at the instance when angle speeds of the joint axles 26 and 28 in the direction of torques applied by the servomotors 30 and 32 exceed a predetermined value, and in turn the application of torques will be stopped.

Thereby, the training device 10 can accurately determine the instance when the muscular forces of a limb of the user 20 exceed their peaks, and thus, it can more accurately measure the maximum muscular force. Further, the training device 10 can measure the maximum muscular forces of a limb of the user 20 more safely without applying an excessive load to the user 20.

Subsequently, an alternative embodiment to which the present invention is applied will be described. Like components or parts are denoted with the same reference numerals throughout the specification and drawings, and a repetitive description thereon will be omitted just for simplicity.

In the previous embodiment, a load at the time when an angular rate of the joint axle exceeds a predetermined value is determined as the maximum muscular force. In the alternative embodiment, a change in posture of the user 20 may be attributable to the aforementioned first and second factors in some cases, measurement may be stopped when the angular rate of the joint axle excessively increases.

A change in posture of the user 20 attributable to those two factors occurs when force generated by the robot arm 12 of the training device 10 is small in the initial stage where the user 20 starts exerting his or her force. Accordingly, the force exerted by the user 20 has a reserve capacity for the maximum muscular force, and thus, the user 20 can restore to the original posture.

Consequently, the training device 10 in the alternative embodiment displays a change in posture of the user 20 himself or herself on a display 48, FIG. 2, connected to the controller 34 to show it to the user 20 and causes the user 20 to be conscious of maintaining himself or herself in a given posture. Thereby, the user 20 can control change in posture within a given range.

Further, the training device 10 in the alternative embodiment nullifies monitoring of a joint angular rate for determining the maximum muscular force within a given range of amount of change in joint angle. For example, in a range where a change in joint angle is two angular degree from the initial position at start measurement, the device 10 does not perform determination of the maximum muscular force based on the joint angular rate. Thereby, erroneous determination in the case of change in posture of the user 20 attributable to the first and second factors can be reduced.

In this way, in the alternative embodiment, the training device 10 nullifies monitoring the angular rates of the joint axles in order to determine the maximum muscular force of the user 20 within a predetermined range of change in angles of the joint axles. More specifically, the controller 34, when the angular change from the default position of the joint axles 26 and 28 has exceeded a predetermined range, records as the maximum muscular force of the upper or lower limb of the user 20 a torque value at the instance when the angular rates of the joint axles 26 and 28 in the direction of torques applied by the servomotors 30 and 32 have exceeded the predetermined value, and will then stop applying torques.

Further, within a predetermined range of angular change from the default position of the joint axles 26 and 28, the controller 34 does not record a torque value at the instance when the angular rates of the joint axles 26 and 28 in the direction of the torques applied by the servomotors 30 and 32, and does not stop applying torques at that instance. Thereby, the training device 10 can reduce erroneous determination in the state of an output of the robot arm 12 after the start measurement being low, and thus can reduce the burden on the user 20.

In addition, the training device 10 in the two embodiments described is mainly directed to the case of measuring the muscular force of the user 20. The training device 10 can also be used to apply loads on a limb of the user 20 for training the muscular force. Also in case of training, like in case of measurement, exceeding the limit of the muscular force of the user 20 is not desirable because it results in application of an excessive load on the user 20. However, when the training device 10 is used, it is possible to more accurately measure the maximum muscular force of a limb of the user 20 even during training. Thereby, the training device 10 can modify a load applied on the user 20 to be an appropriate value in the training.

Subsequently, modeling of the training device 10 will be described. When measurement and/or training of the muscular force of the user 20 is performed by the training device 10 for the first time, it is necessary to measure an axial torque for supporting the own weight of a limb and the own weight of the robot arm 12 in a state of the user 20 wearing the robot arm 12, i.e. an axial torque for supporting the own weight. The axial torque for supporting the own weight is measured with torque sensors 58 and 60, FIG. 3, mounted on the joint axles 26 and 28 of the robot arm 12, respectively, and is evaluated in connection with the joint angles.

Further, the posture of the user 20 at the time of measuring the axial torque for supporting the own weight is desirable within the range of motion of the respective joints, i.e. it is desirable to cover the range of motion. The posture, for example when the range of motion of the hip joint is divided into six sub-ranges and the range of motion of the knee joint into six sub-ranges, is set by combining seven degrees of angle in the hip joint and seven degrees of angle in the knee joint.

In regard to the limbs of the human being, the maximum extension angle of the knee joint for example in a state of the hip joint being in the maximum flexion is smaller than the maximum extension angle of the knee joint in a state of the thigh being in approximately alignment with the body. As just described, the hip and knee joints do not have the respective own independent freedoms. Thus, even when the posture is at seven degrees of angle in the hip joint and at seven degrees of angle in the knee joint, measurable posture is smaller in number than the number "49" in the entire range of motion. These postures are referred to as the first, the second measuring posture and so on.

Subsequently, the procedure will be described for measuring an axial torque for supporting the own weight of the upper or lower limb to be measured and the own weight of the robot arm 12. The training device 10 controls the angles of the joints to adjust the posture of the robot arm 12 to a posture easy for the user 20 to wear it. Then, the user 20 wears the mounting fixtures 14 and 16 of the robot arm 12 on the upper or lower limb. The operator of the training device 10, after giving instructions to the user 20 to relax his or her upper or lower limb to be measured, controls the angle of the joint to set up the posture for starting measurement of an axial torque for supporting the own weight of the robot arm 12, i.e. the first measuring posture.

Then, at the time when the measuring posture has become stable, the measurement is performed with the torque sensors 58 and 60 of the joint axles 26 and 28, and thereafter, the measured axial torque is recorded together with the joint angle. Subsequently, the training device 10 controls the joint angle to thereby adjust the posture of the robot arm 12 to the second measuring posture. In a manner similar to the case of the first measuring posture, at the time when the measuring posture has become stable, an axial torque is measured with the torque sensors of the joint axles 26 and 28, and the joint angle and the measured axial torque are recorded.

In this way, the posture of the robot arm 12 is changed in turn, and also in each posture after the third measuring posture, like in the case of the first and second measuring postures, an axial torque of the joint axles 26 and 28 are measured, and the joint angle and the measured axial torque are recorded. Then, when the measurement of the axial torques was completed for the joint axles 26 and 28 in the all measuring postures, the angle of the joint is controlled to adjust the posture of the robot arm 12 to a posture easy for the user 20 to take off the mounting fixtures 14 and 16 by the joint angle of control with the controller 34.

According to the procedure described above, it is possible to obtain a relationship between the angle of the joint and the axial torque of the own weight. The torque thus measured is a torque required for supporting the own weight of the upper or lower limb of the user 20 to be measured and the own weight of the robot arm 12.

The alternative embodiment described above is directed to the degree of angle for the measuring posture set at seven degrees of angle in both hip and knee joints. The invention may not be limited to the specific case of seven degrees of angle, but the degree of angle in the hip joint may be different from the degree of angle in the knee joint.

A load actually applied on the muscles in measurement and/or training of muscular force is a torque obtained by deducting the afore-mentioned torque for supporting the own weight, i.e. an own weight supporting axial torque, from an axial torque generated by the robot arm 12. However, in case of executing measurement and/or training of muscular force, the user 20 may often take a posture other than the measuring postures described above. Thus, the training device 10 is required to estimate an axial torque for supporting the own weight in all the postures based on the measured result.

Figure 9A:
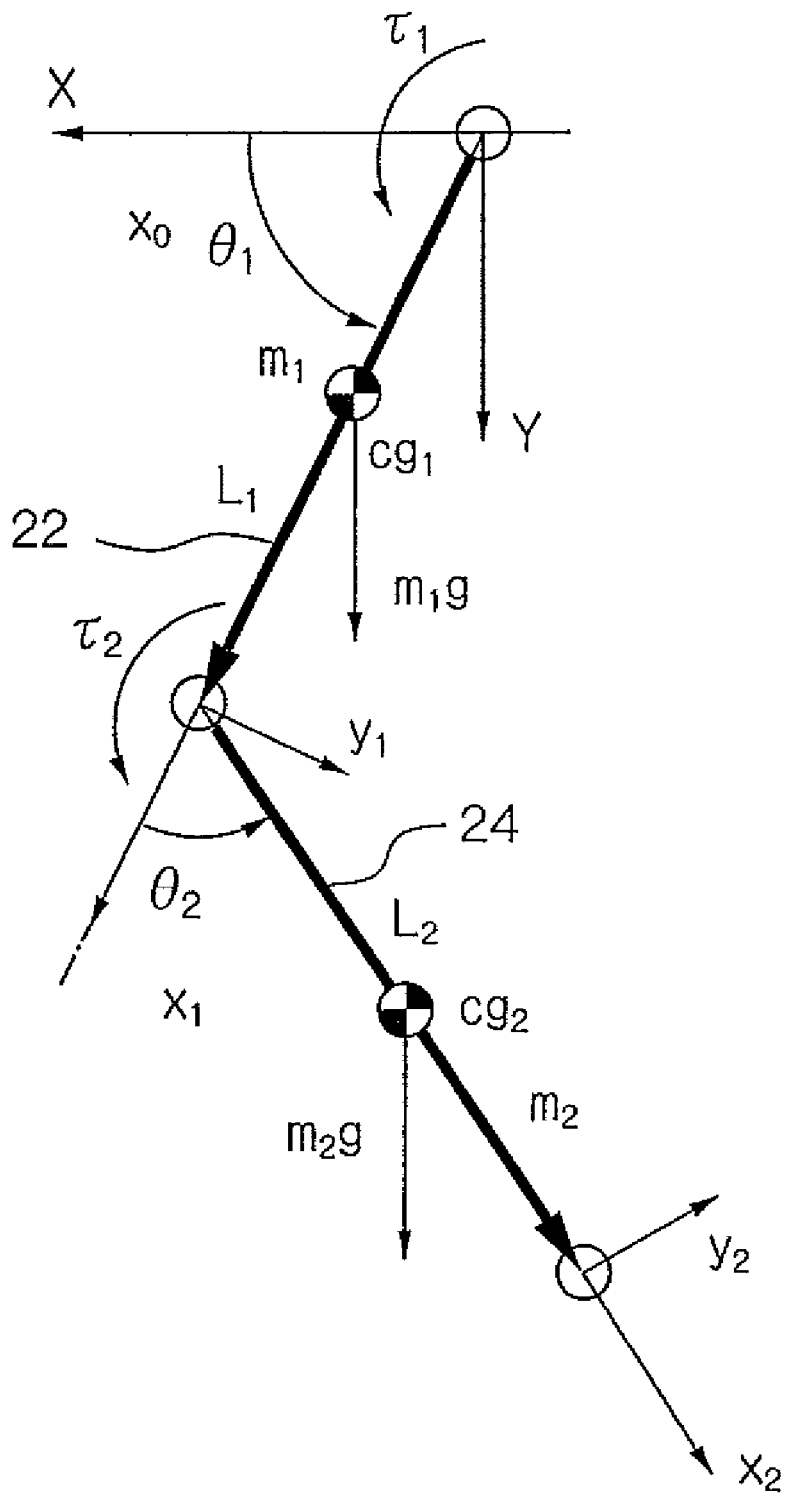
FIG. 9A shows a relationship between parameters included in two modeled links in the training device shown in FIG. 1A.
Figure 9B:
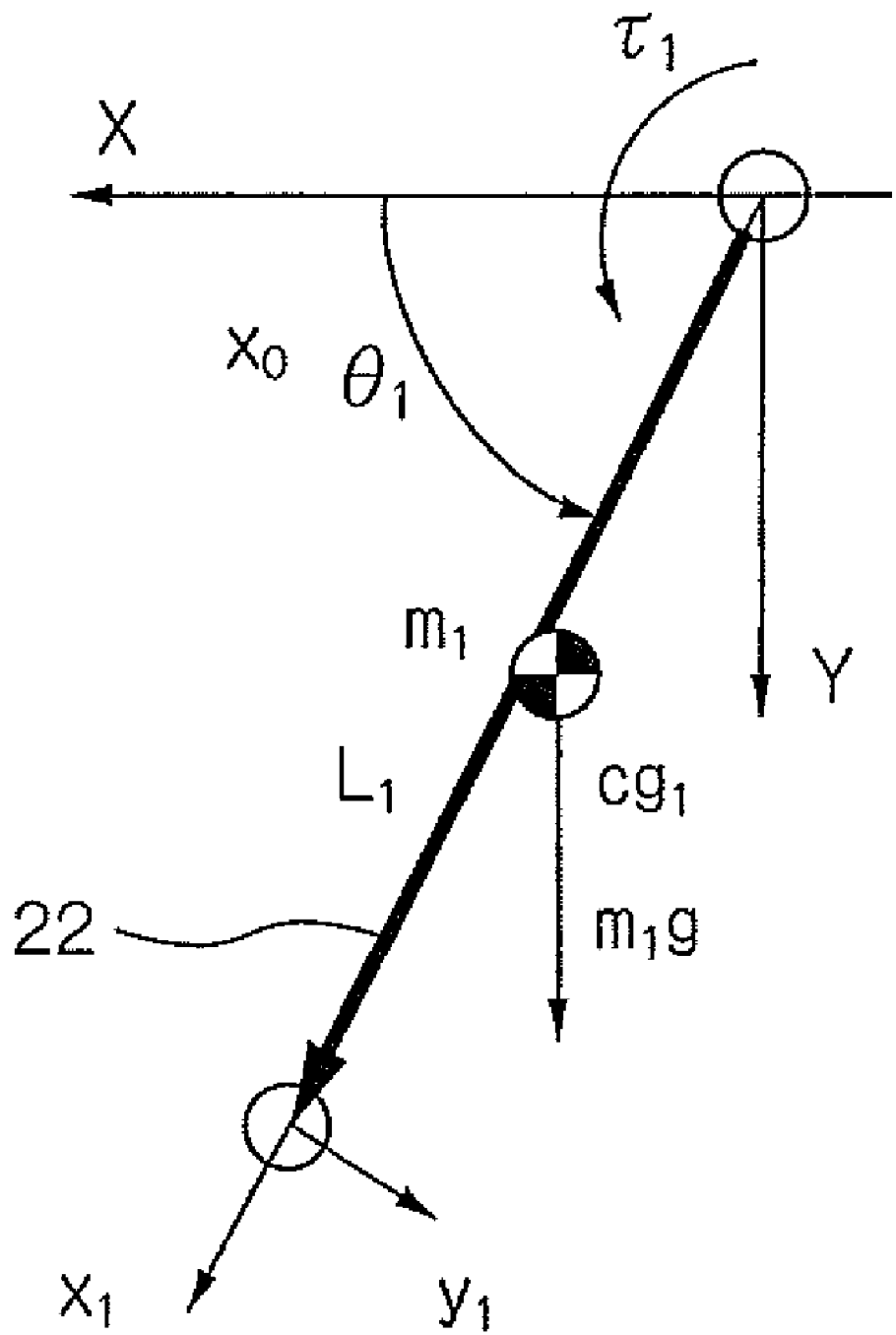
FIG. 9B shows a relationship between parameters included in one modeled link shown in FIG. 1A.
Figure 9C:
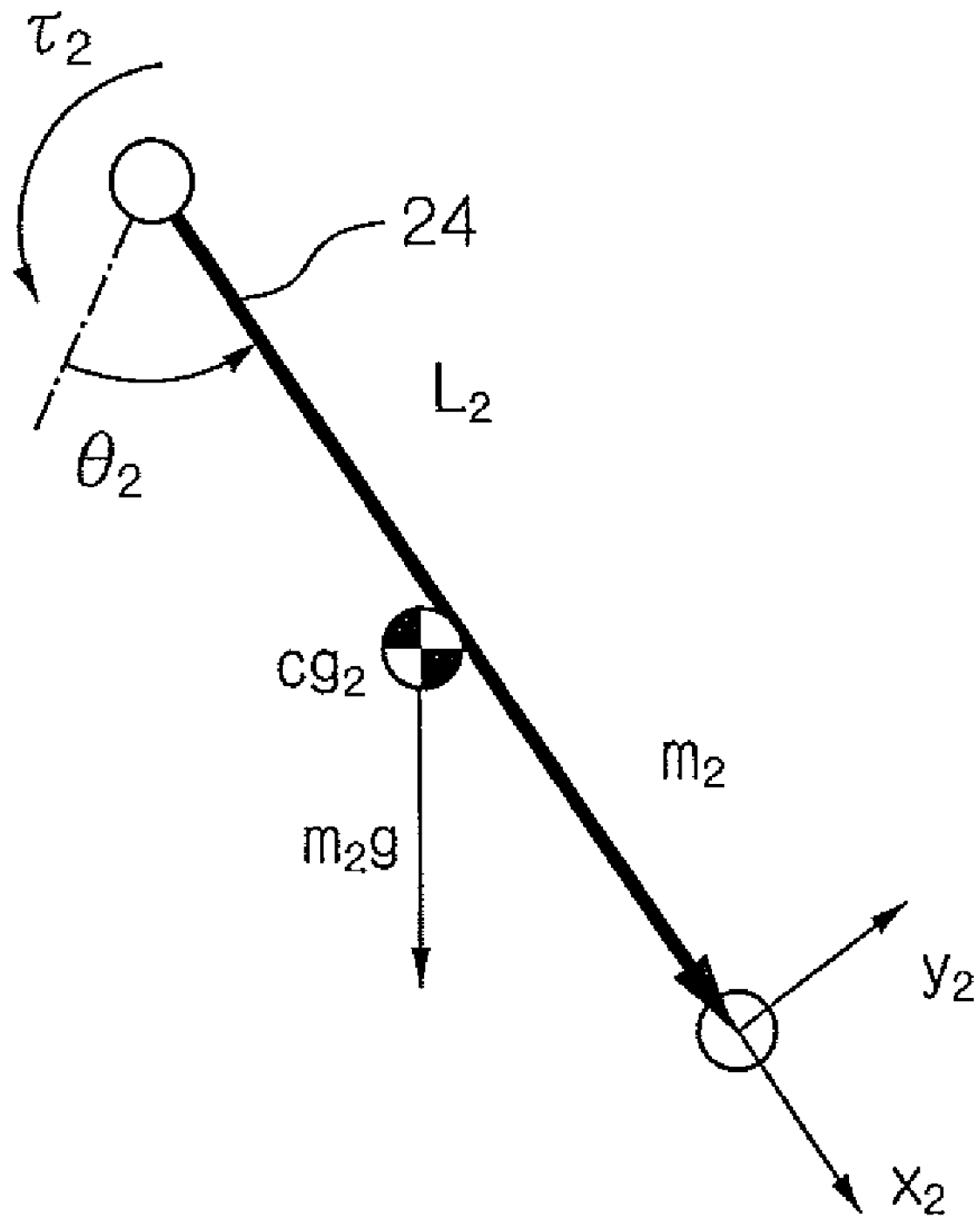
FIG. 9C shows a relationship between parameters included in the other modeled link shown in FIG. 1A.

Subsequently, a method for estimating an axial torque for supporting the own weight in optional postures of the user 20 will be described. The robot arm 12 having two degrees of freedom, using the links 22 and 24, is modeled as shown in FIGS. 9A, 9B and 9C. In FIGS. 9A, 9B and 9C, the entire coordinate system is set on coordinate X in the horizontal direction, coordinate Y in the direction of gravitational force and coordinate Z upward from the plane of the figures. The coordinate system X-Y-Z is a right-handed coordinate system.

Further, torques $\tau_1$ and $\tau_2$ are generated in the hip and knee joints, respectively, by the own weights of the links 22 and 24. The length and mass of the link 22 are $L_1$ and $m_1$, respectively, and the length and mass of the link 24 are $L_2$ and $m_2$, respectively.

Still further, at the distal ends of the link 22 and 24, respective coordinate systems are set. The origin of the coordinate system of the link 22 is set at the distal end of the link 22. An axis $x_1$ is set in the direction from the hip joint axle to the knee joint axle, i.e. on an extension line of the link 22. The direction of an axis $z_1$ is set in the direction same as the axis Z, and an axis $y_1$ is set so as to form a right-handed coordinate system with the axis $x_1$, $y_1$, $z_1$. Correspondingly, in the coordinate system of the link 24, the origin of the coordinate is set at the distal end of the link 24 and axes $x_2$, $y_2$, $z_2$ are set. Further, an angle $\theta_1$ of the hip joint is set equal to an angle formed of the axes X and $x_1$, while an angle $\theta_2$ of the knee joint is set equal to an angle formed of the axes $x_1$ and $x_2$.

In FIGS. 9A, 9B and 9C, the gravity center of the link 22 is denoted with $cg_1$ and the location of the gravity center $cg_1$ is set in a location $(x_{cg1}, y_{cg1})$ viewed on the coordinate system $x_1$-$y_1$. Correspondingly, the gravity center of the link 24 is denoted with $cg_2$ and is set in a location $(x_{cg2}, y_{cg2})$ viewed on the coordinate system $x_2$-$y_2$, where a symbol g is the acceleration of gravity.

It can be seen that the torques $\tau_1$ and $\tau_2$ are represented by expressions (1) and (2) from the coordinates of the direction x of the gravity centers $cg_1$ and $cg_2$.

$$\tau_1 = m_1 g\{(L_1 + x_{cg1})\cos\theta_1 - y_{cg1}\sin\theta_1\} + \\ m_2 g\{L_1\cos\theta_1 + (L_2 + x_{cg2})\cos(\theta_1 + \theta_2) - y_{cg2}\sin(\theta_1 + \theta_2)\} \\ = \{m_1 g(L_1 + x_{cg1}) + m_2 g L_1\}\cos\theta_1 - m_1 g y_{cg1}\sin\theta_1 + \tau_2 \quad (1)$$

$$\tau_2 = m_2 g(L_2 + x_{cg2})\cos(\theta_1 + \theta_2) - m_2 g y_{cg2}\sin(\theta_1 + \theta_2) \quad (2)$$

From the above, a relationship between the torques $\tau_1$ and $\tau_2$ generated by the measured joint angle and the own weights of the link 22 and 24 is a linear combination of cosine and sine of the angles $\theta_1$ and $\theta_1 + \theta_2$, and thus, approximate expressions, such as expressions (3) and (4) can be formed as below:

$$\tau_1 = A\cos\theta_1 + B\sin\theta_1 + C + \tau_2 \quad (3)$$

$$\tau_2 = D\cos(\theta_1 + \theta_2) + E\sin(\theta_1 + \theta_2) + F \quad (4)$$

In the expressions, coefficients A to F are determined by a linear multiple regression analysis. The torque $\tau_1$ is a linear combination of the cosine and sine of the angle $\theta_1$ by deducting the torque $\tau_2$ from the torque $\tau_1$ measured in the same measuring posture.

The controller 34 of the training device 10 records the coefficients calculated by the linear multiple regression analysis in a nonvolatile storage medium serving as the recorder. When the user 20 performs measurement or training of muscular force, the controller 34, based on expressions (3) and (4), which are approximate expressions, adds the result of calculating a torque generated by the own weight from the joint angle to the torque target value to thereby renew the target value of the servomotors 30 and 32.

For each user, the result of measuring the own weight or the coefficients A to F calculated by the approximate expressions is recorded in a nonvolatile memory, and when performing measurement or training of muscular force, an appropriate user can read out his or her measured result, thus refraining from measuring the own weight each time.

In the operation of the alternative embodiment, the training device 10, before starting a measurement and/or training of muscular force, obtains beforehand data indicating the relation between the own weight supporting axial torque generated in the joint axles 26 and 28 by the own weight of a limb of the user 20 and the own weight of the robot arm 12 and the angles of the joint axles. Then, before starting measurement and/or training of muscular force, the training device 10 corrects a value of the axial torque based on the obtained data. Thereby, the training device 10 can apply an intended load accurately on a limb of the user 20.

Figure 11:
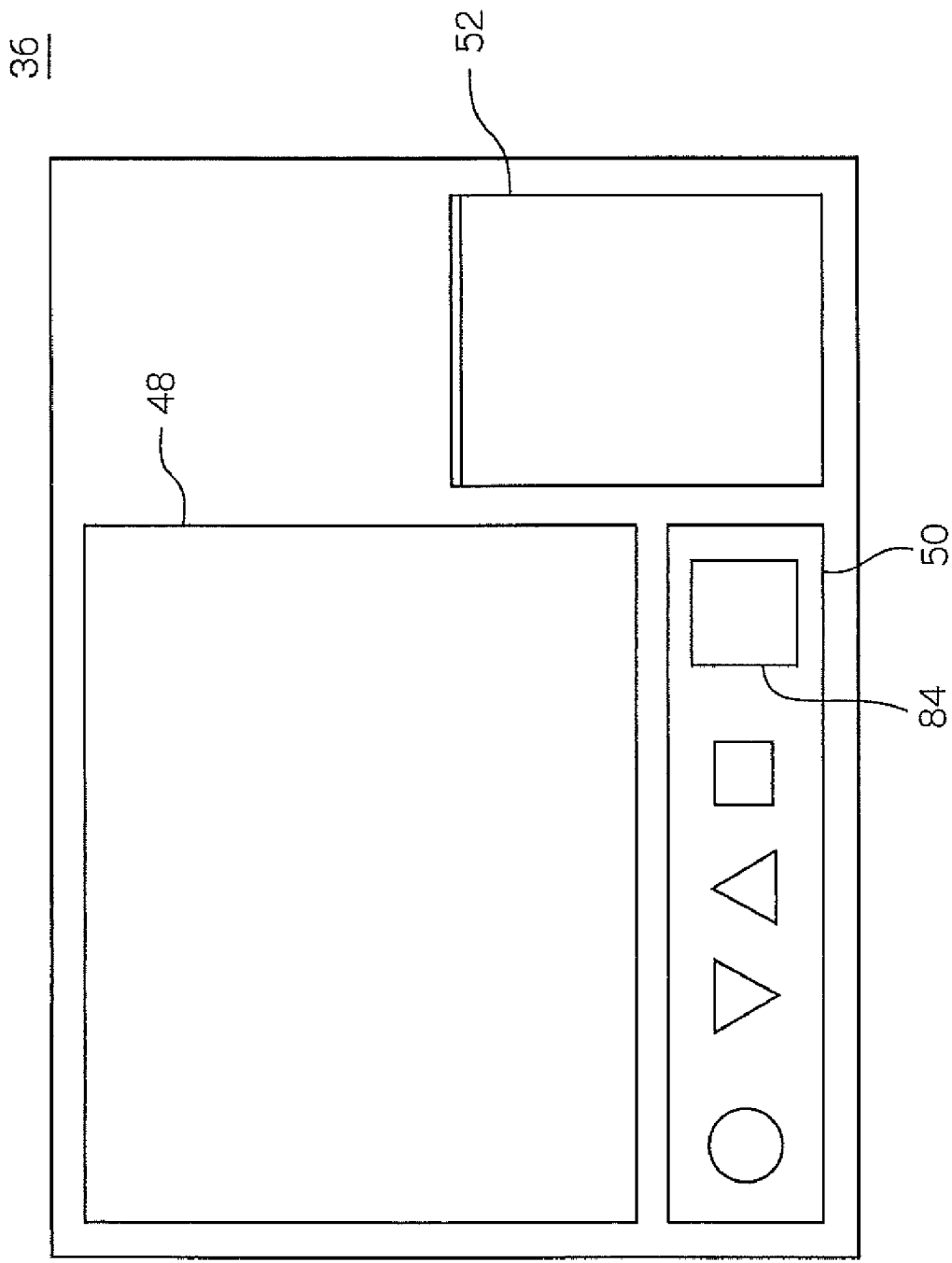
FIG. 11 is a plan view showing the layout on the input operation panel of the control box shown in FIG. 1A.

Now, another alternatively embodiment will be described. In this alternative embodiment, as shown in FIG. 11, the training device 10 further comprises a stop switch 84 connected to the controller 34. Thus, the user 20 can optionally manipulate the stop switch 84 in order to stop the measurement of own weight.

Figure 10:
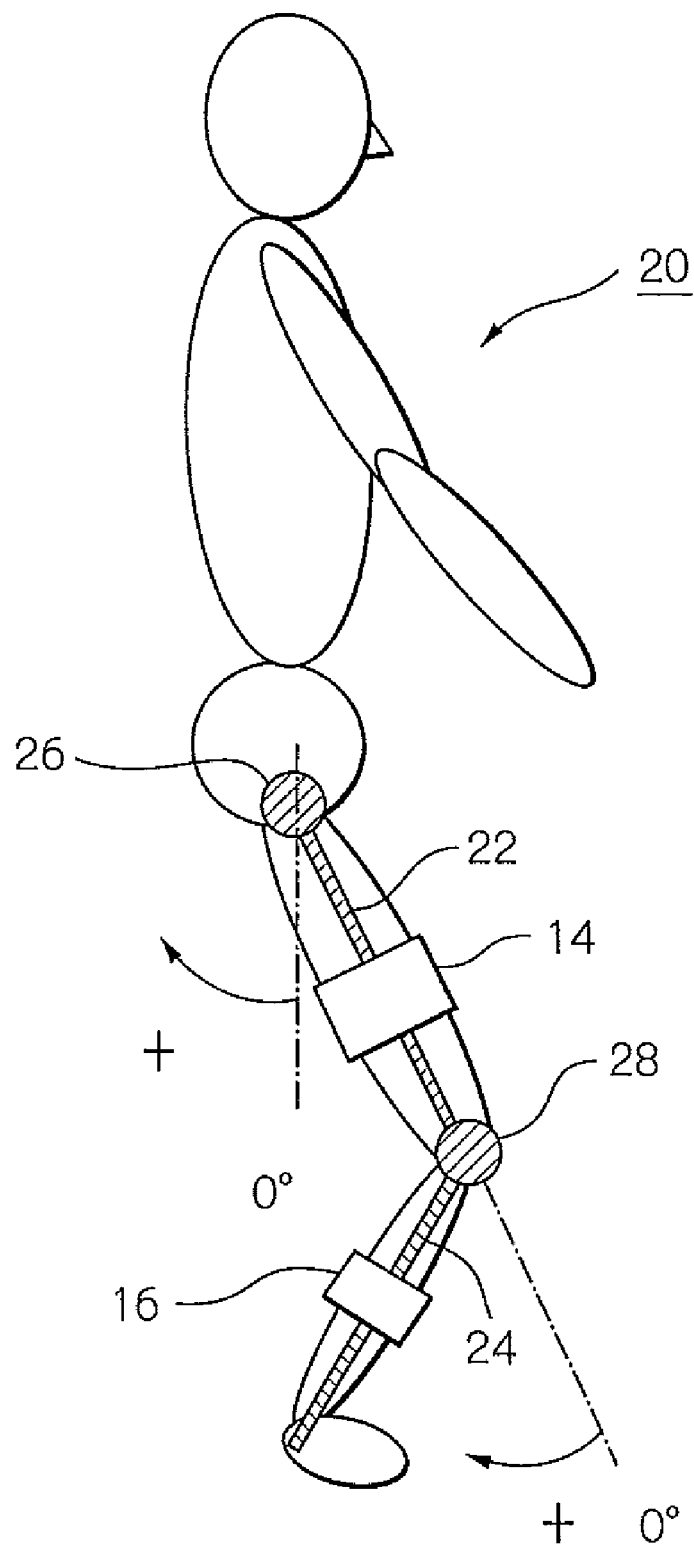
FIG. 10 shows the center of the range of motion of the hip and knee joints of the trainee in the training device shown in FIG. 1A.

By the way, the first measuring posture in measurement of an axial torque of own weight is set in such a way that the angles of the hip and knee joints are in the range of motion of the hip and knee joints, i.e. they are equal to the angles estimated to be in the center of the range of motion. When the user 20 is physically normal, the center of the range of motion of the hip and knee joints is at about minus 45 angular degrees for the hip joint and at about plus 77 angular degrees for the knee joint as shown with the directions in FIG. 10.

Figure 12:
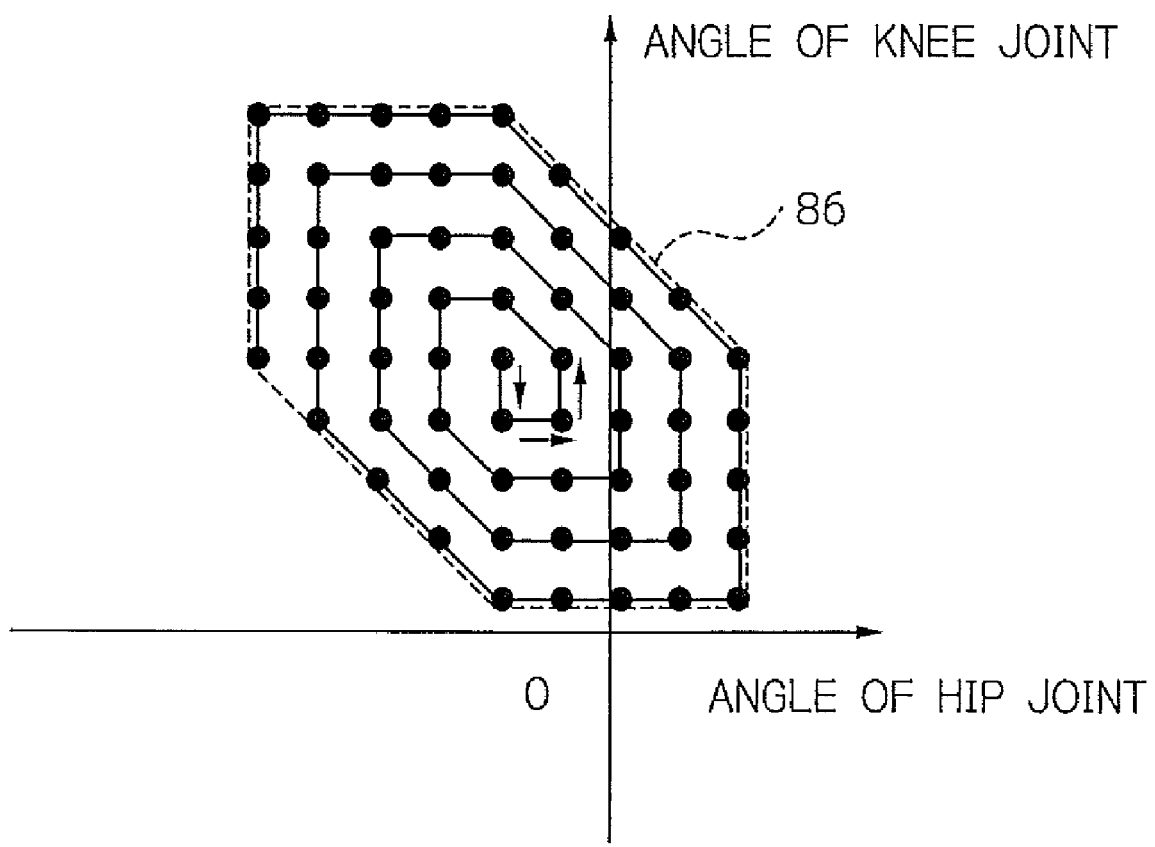
FIG. 12 shows the range of motion of the hip and knee joints of the trainee in the training device shown in FIG. 1A.

Further, the motion in the lower limb of the human being, i.e. the range of motion of the hip and knee joints may fall in the hexagonal range as shown with a dotted line 86 in FIG. 12. Thus, the measuring posture in measurement of an axial torque of own weight starts with the first measuring posture set to be in the center of the range of motion, and is set in turn to the second measuring posture, the third measuring posture and so on to enlarge the hexagon gradually in a spiral manner.

However, there is individual difference in the extent of the range of motion. For this, a certain user can set himself or herself to the respective measuring postures to meet the hexagonal range as shown with a dotted line 86 in FIG. 12, whereas another user may be low in flexibility of the hip and knee joints. In other words, there is a possibility that the range of motion is narrower than the hexagonal range shown with the dotted line 86 in FIG. 12.

Thus, the training device 10 in the instant alternative embodiment comprises, as shown in FIG. 11, the stop switch 84 provided on the input operation panel 52 of the input/output box 36. The user 20 can thus manipulate the stop switch 84 to stop measurement of an axial torque for supporting the own weight, when he or she feels pain or unusual in the lower limb during the period of changing his or her measuring posture in turn in the measurement of an axial torque for supporting the own weight. Accordingly, the user 20 would not take uncomfortable posture, and thus his or her lower limb is not injured.

Figure 13:
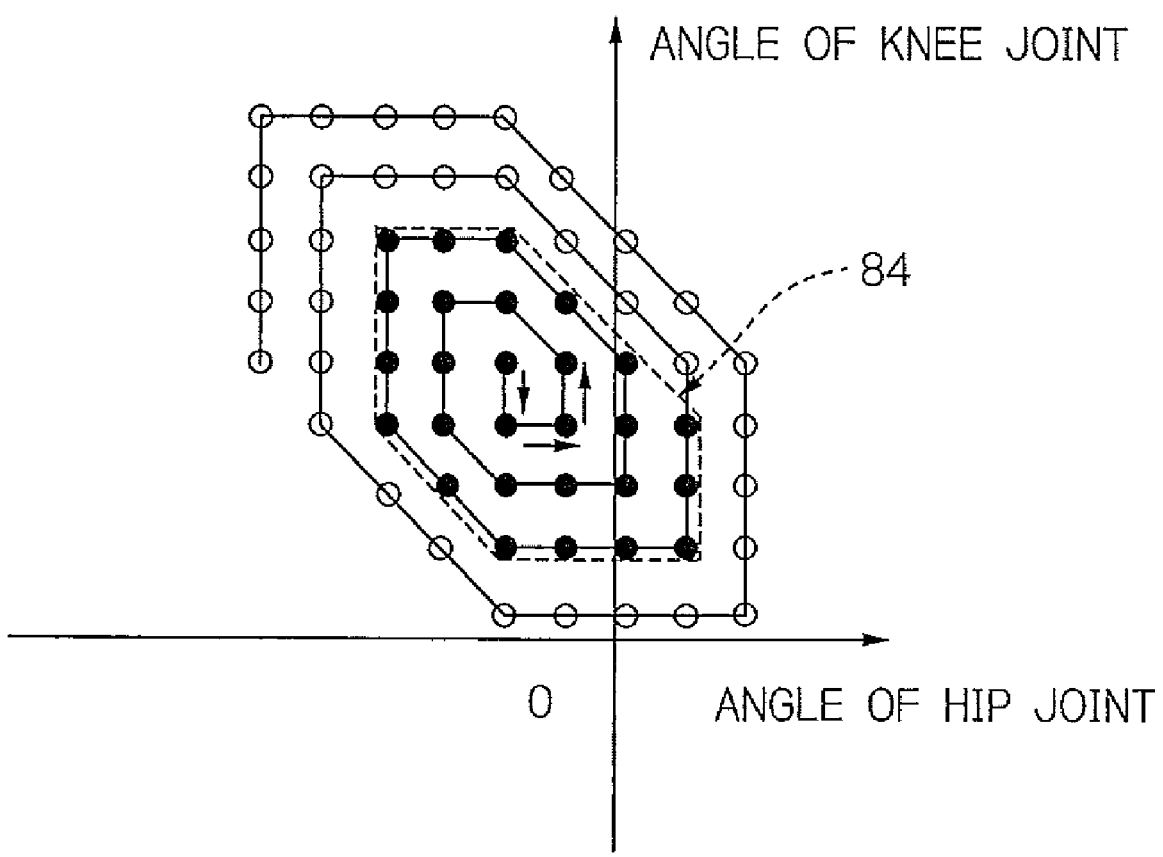
FIG. 13 shows the range of motion of the hip and knee joints of the trainee in the training device shown in FIG. 1A.

Further, when the controller 34 of the training device 10 detects that the stop switch 84 has been manipulated, it stops measurement of an axial torque for supporting the own weight and restores the posture of the robot arm 12 to the first measuring posture. Subsequently, when the stop switch 84 has been manipulated to stop the measurement of an axial torque for supporting the own weight before the completion of the measurement of an axial torque for supporting the own weight in all the postures, the controller 34, as shown in FIG. 13, confines the range of motion 58 of the hip and knee joints to be within the hexagonal range surrounding the measuring postures in which the measurement has been made before the stoppage.

When the joint angle of the robot arm 12 has deviated from the range of motion 86 of the hip and knee joints having the limited joint angle of the robot arm 12 in measurement and/or training of muscular force, the controller 34 changes the control of the robot arm 12 from the torque control over to the joint angle control to maintain the posture and stops the measurement and/or training of muscular force.

In this way, the training device 10 measures the range of joint motion 86 during measurement of an axial torque for supporting the own weight of a limb of the user 20 and the own weight of the robot arm 12 before the start of measurement and/or training of muscular force. Further, the user 20 can manipulate the stop switch 84 to stop the measurement at his or her own will during the measurement of an axial torque for supporting the own weight.

Thereby, the user 20 can reduce time for measuring a load and own weight. Also, by confining the posture of the robot arm 12 within the measured range of joint motion 86, the user can safely perform measurement and/or training of muscular force.

In addition, the above description is directed to an approximate expression for an axial torque for supporting own weight being a linear combination of cosine and sine. However, assuming that coordinates $y_{cg1}$ and $y_{cg2}$ of the centrobaric position corresponding to the thigh and the lower limb are regard as being zero, a coefficient of an approximate expression can be obtained by a single regression analysis with an assumption of a coefficient of sine being zero. Thereby, there is no need of calculating sine, and therefore the computational effort can be reduced, even in an application where the controller 34 is implemented by a micro-controller without having a numeric processor.

Well, bike riding motion as a function for training the lower limb in the training device 10 will be described. In such a case, the user 20 wears the respective training devices 10 on his or her right and left legs. Bike riding motion is a circular motion, in which the distal ends of the legs are fastened on the pedals to turn the crank of the bike.

Figure 14A:
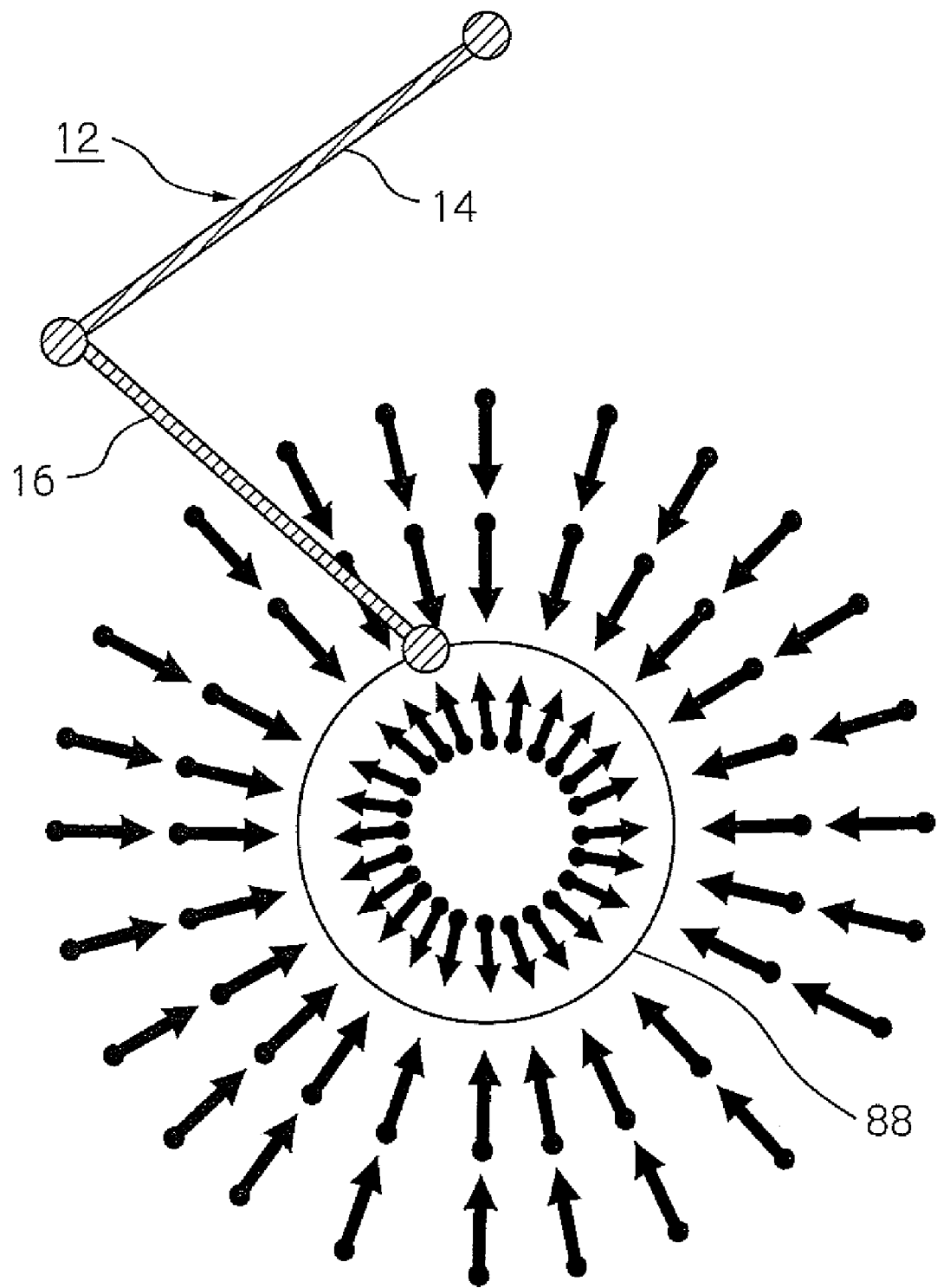
FIG. 14A shows a relationship between the circular or bit of the distal end of a robot arm and the forces in the training device shown in FIG. 1A.
Figure 14B:
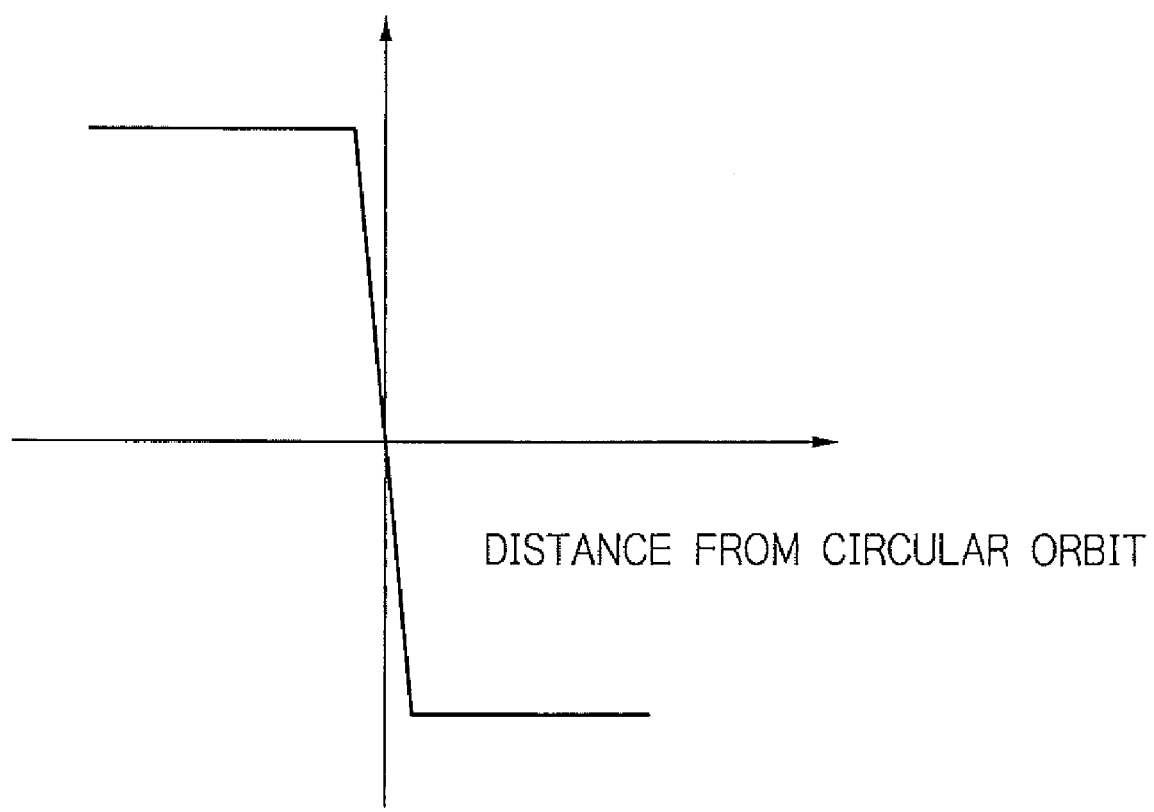
FIG. 14B shows a relationship between the distance from the circular orbit and the restorative force therefrom in the training device shown in FIG. 1A.

Thus, as shown in FIG. 14A, a virtual circular orbit 88 is presumed. When the distal end of the robot arm 12 corresponding to the distal ends of the legs of the user 20 has got away from the circular orbit 88 in the radial direction, the robot arm 12 generates restorative force, as shown with arrows. The restorative force restores the distal end to the circular orbit 88. The magnitude of the restorative force varies depending on distance from the circular orbit 88 of the distal end of the robot arm 12, as shown in FIG. 14B. Thereby, the user 20 is forced to perform motion of drawing the circular orbit 88 with the distal ends of his or her legs.

If the orbit of the distal end is fixed to the circular orbit 88, the controller 34 calculates beforehand a relation between the joint angle and the force generated in the root arm 12 as the relation between the joint angle of the robot arm 12 and a torque generated by the joint axle. The controller 34 can store the calculated result in a reference table in the memory. By referencing this reference table, when training the muscular force, the controller 34 can reduce operational burden incurred on the arithmetic operation.

It is disclosed in the Japanese '137 publication stated earlier that in the case of training a group of mono-articular flexors f1 on the flexor aspect of hip joint, it is effective to perform the training at a ratio of 1:1 in respect of the direction a, in which activated are a group of mono-articular flexors f1 on the flexor aspect of hip joint, a group of mono-articular flexors e2 on the extensor aspect of knee joint and a group of bi-articular flexors e3 on the extensor aspect of thigh as well as in respect of the direction c, in which activated are a group of mono-articular flexors f1 on the flexor aspect of hip joint, a group of mono-articular flexors f2 on the flexor aspect of knee joint and a group of bi-articular flexors f3 on the flexor aspect of thigh.

In the case of bike riding, a load in the training of a group of mono-articular flexors f1 on the flexor aspect of hip joint is caused to be varied depending on posture of the robot arm 12. The robot arm 12 shown in FIG. 15, which shows the case of bike riding, is in a state of being in the tangential direction of the circle of a circular orbit 88 drawn by the distal end of the user 20 being coincided with the direction a, in which activated are a group of mono-articular flexors f1 on the flexor aspect of hip joint, a group of mono-articular flexors e2 of the extensor aspect of knee joint and a group of bi-articular flexors e3 on the extensor aspect of thigh.

Figure 15:
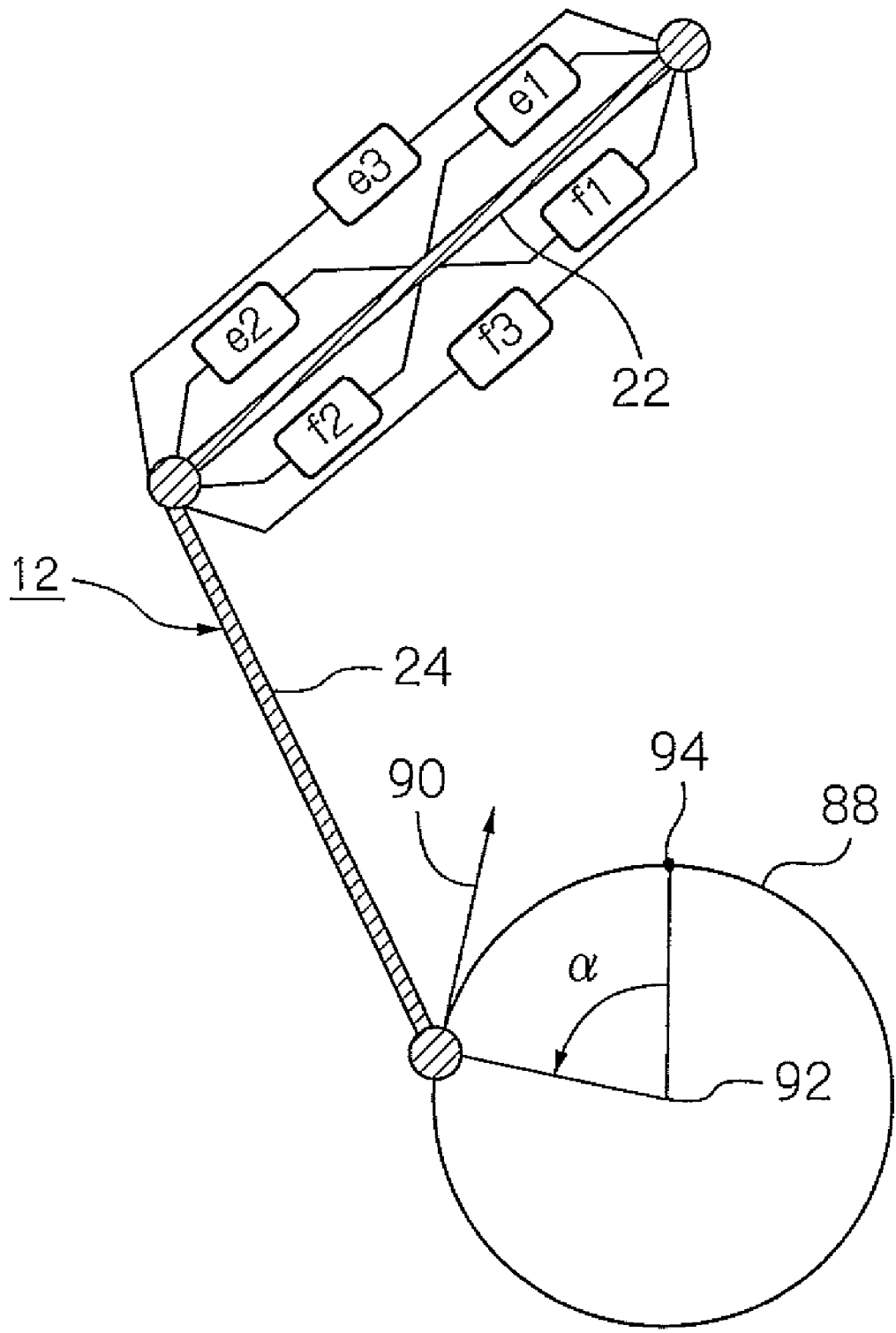
FIGS. 15 and 16 schematically show the posture of the robot arm in the training device shown in FIG. 1A.

An arrow 90 in FIG. 15 indicates the tangential direction of the circle, and is opposite to the direction a to indicate the direction of a training load generated by the robot arm 12. Further, the angle α is an argument representing the position of the distal end of the robot arm 12 corresponding to the distal end of the leg of the user 20 on the polar coordinates where the center of the circular orbit 88 is regarded as the origin, or pole, 92, and indicates the measure of the central angle from a starting point 94, the peak of the circle, to the distal end of the robot arm 12.

Figure 16:
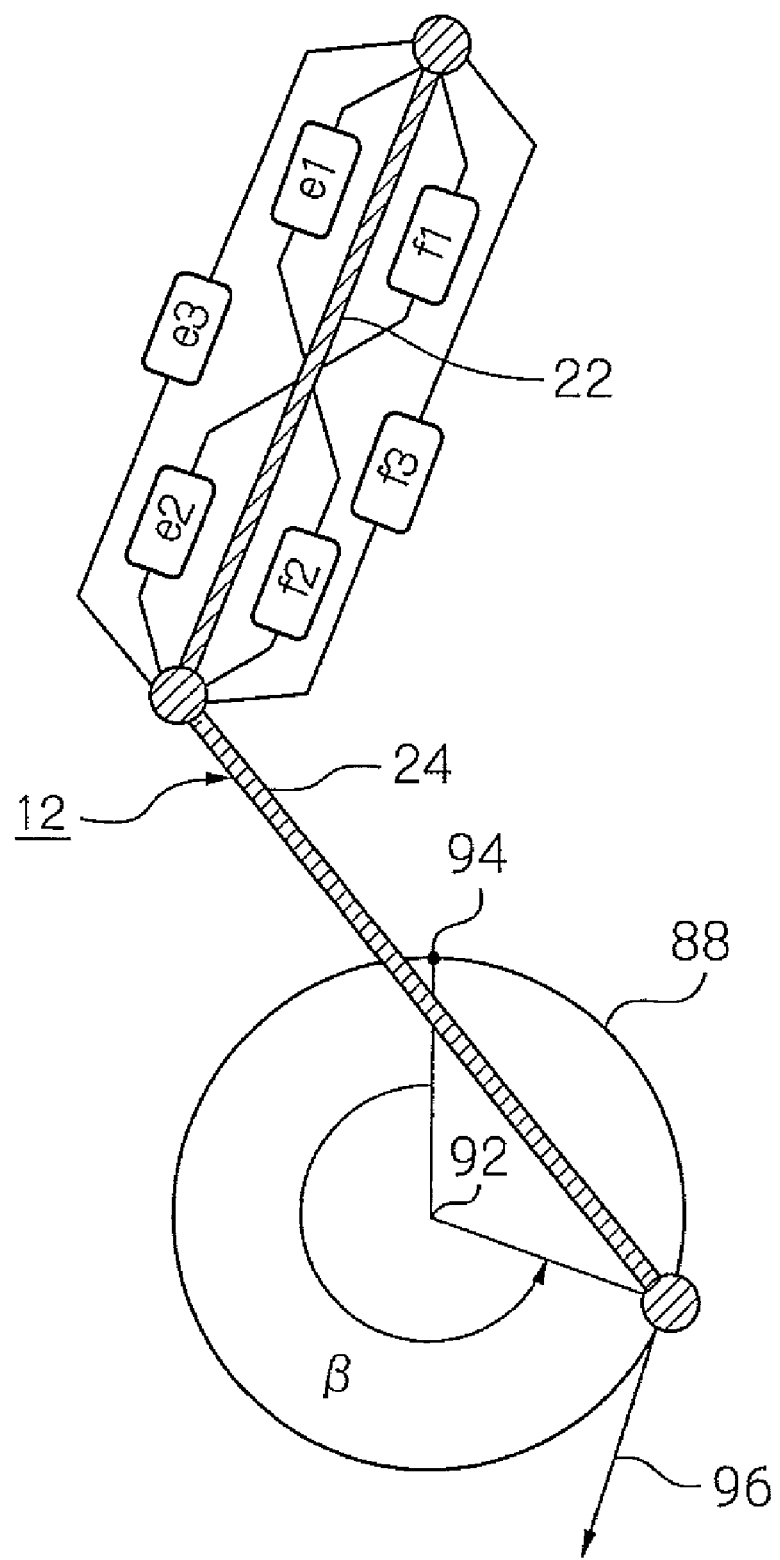

The robot arm 12 shown in FIG. 16, which shows the case of bike riding, is in a state of being in the tangential direction of the circle of the circular orbit 88 drawn by the distal end of the leg of the user 20 being coincided with the direction c, in which activated are a group of mono-articular flexors f1 on the flexor aspect of the hip joint, a group of mono-articular flexors f2 on the flexor aspect of the knee joint and a group of bi-articular flexors f3 on the flexor aspect of the thigh.

An arrow 96 in FIG. 16 indicates also the tangential direction of the circle, and is opposite to the direction c to indicate the direction of a training load generated by the robot arm 12. The angle β is the argument representing the position of the distal end of the robot arm 12 corresponding to the distal end of the leg of the user 20 ion the polar coordinates where the center of the circular orbit 88 is regarded as the origin, or pole, 92, and indicates the measure of the central angle from a starting point 66 to the distal end of the robot arm 12.

In the instant alternative embodiment, when the posture of the robot arm 12 mounted on the legs of the user 20 is in positions shown in FIGS. 15 and 16, i.e. when the distal end of the user 20 has reached the positions of the arguments α and β on the circular orbit 88, the robot arm 12 generates a load as a training load in the circumferential direction shown with the arrow 96 and applies the load to the leg of the user 20.

Figure 17:
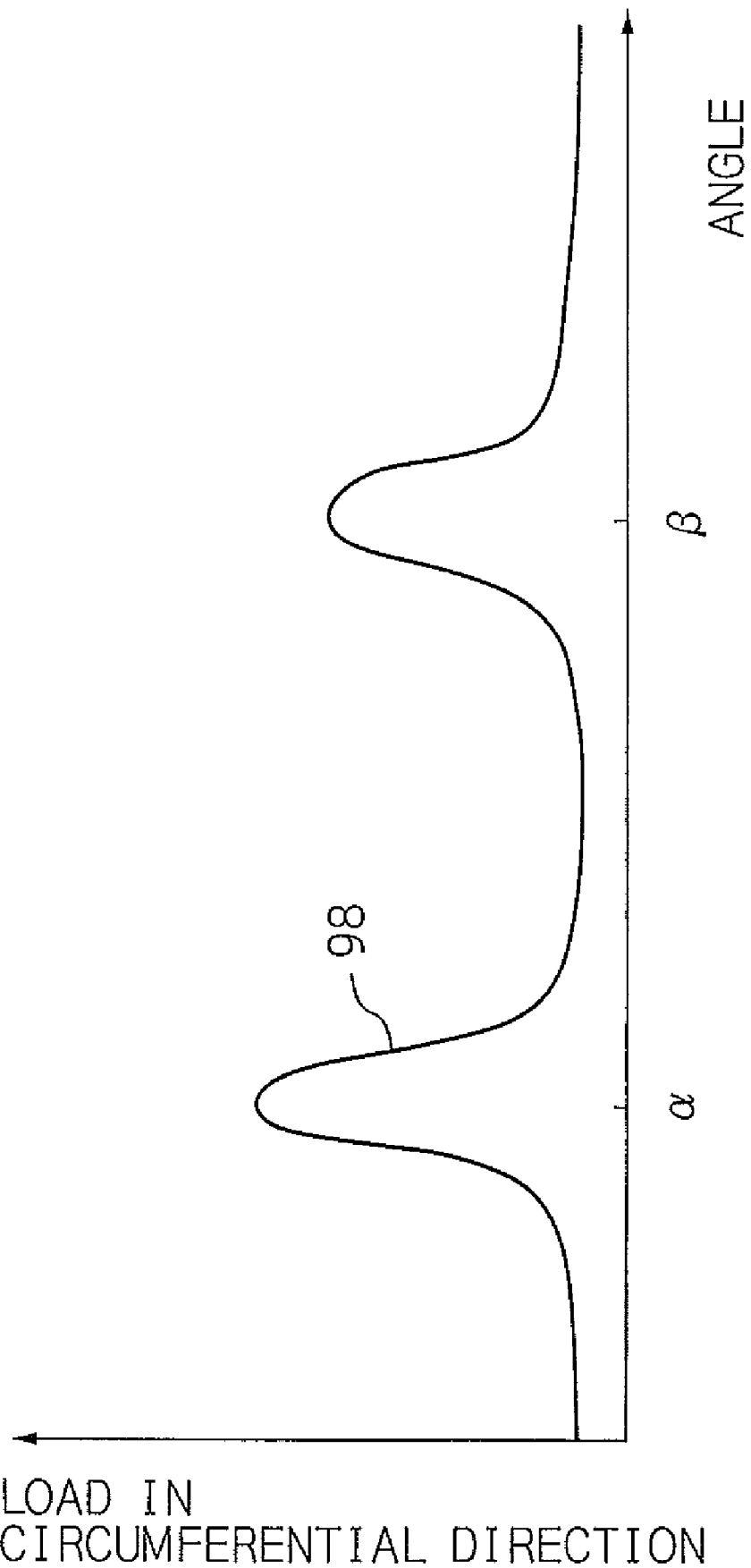
FIG. 17 shows a relationship between the posture of the robot arm and change in load on the training device shown in FIG. 1A.

In other words, a load in the circumferential direction is applied to the leg of the user 20, when the distal end position of the user 20 comes to the angles α and β from the starting point 94, as shown in FIG. 17. In such a case, the controller 34, based on data stored in the reference table, causes the robot arm 12 to generate a load 98 in the circumferential direction shown in FIG. 17. Thereby, the robot arm 12 can alternatively train a group of mono-articular flexors f1 on the flexor aspect of hip joint in the legs of the user 20 as target muscles.

A load actually applied is a combination of a restorative force in the radial direction forcing the user 20 to perform motion in a way of drawing the circular orbit 88 with the distal end of his or her leg shown with the arrow in FIG. 14A and a load in the circumferential direction as a load for training a group of hip joint mono-articular flexors f1 on the flexor aspect of hip joint in the leg of the user 20 shown with the arrows in FIGS. 15 and 16. The load in the circumferential direction can also be added in the reference table after calculated beforehand.

The restorative force in the radial direction is preferable to be sufficiently larger than that in the circumferential direction. In training in the instant alternative embodiment, it is considered in general that an orbit drawn with the distal end of the leg of the user 20 significantly deviates from the circular orbit 88 right after the start training. In such a case, restorative force in the radial direction is applied on the leg of the user 20. However, the user 20 makes the orbit that he or she draws with the distal end of his or her leg gradually closer to the circular orbit 88 according to the repetition of the training. Accordingly, the restorative force in the radial direction applied on the leg of the user 20 gradually reduces and comes close to zero. With such a situation, this restorative force makes the sum of loads applied to the leg close to the load in the circumferential direction.

In addition, the invention is not limited to the case where the distal end of the leg of the user 20 draws the circular or bit 88, but is applicable to any other shapes of orbit. Because, considering that the radial and circumferential directions of the circular orbit 88 are replaced with the directions vertical or tangential to the orbit, an orbit in any other shape may be applied. Further, a training target may be the arm, rather than the leg.

As described above, according to the instant alternative embodiment, an axial torque is generated based on the axial torques of the joint axles shown in a reference table and the angles of the joint axles, by means of which the distal end of the user 20 is maintained to draw a predetermined orbit and a load for training a specified group of muscles of praxis is applied to the leg of the user 20. The user can thereby perform training of a specified group of muscles of praxis effectively, while reproducing an actual motion pattern like that in bike riding in a simulative fashion.

Subsequently, described will be still another alternative embodiment of the training device 10, to which the invention is applied. In the present alternative embodiment, the controller 34 is adapted to classify an axial torque corresponding to a load in the vertical direction of an orbit drawn with the distal end of the user 20, i.e. in the radial direction of the circle, and an axial torque corresponding to a load in the tangential direction of the orbit, i.e. in the circumferential direction of the circle and store them in a reference table.

The load in the direction tangential to the orbit 88 sets a speed in the direction tangential to the orbit 88 in the training to a training speed, for which it represents a coefficient resulting in an monotonic increase by multiplying data stored in the reference table. Thereby, as shown in FIG. 18, a load applied to the leg of the user 20 can be varied according to the speed of the distal end of the leg of the user 20 in the training.

Figure 18:
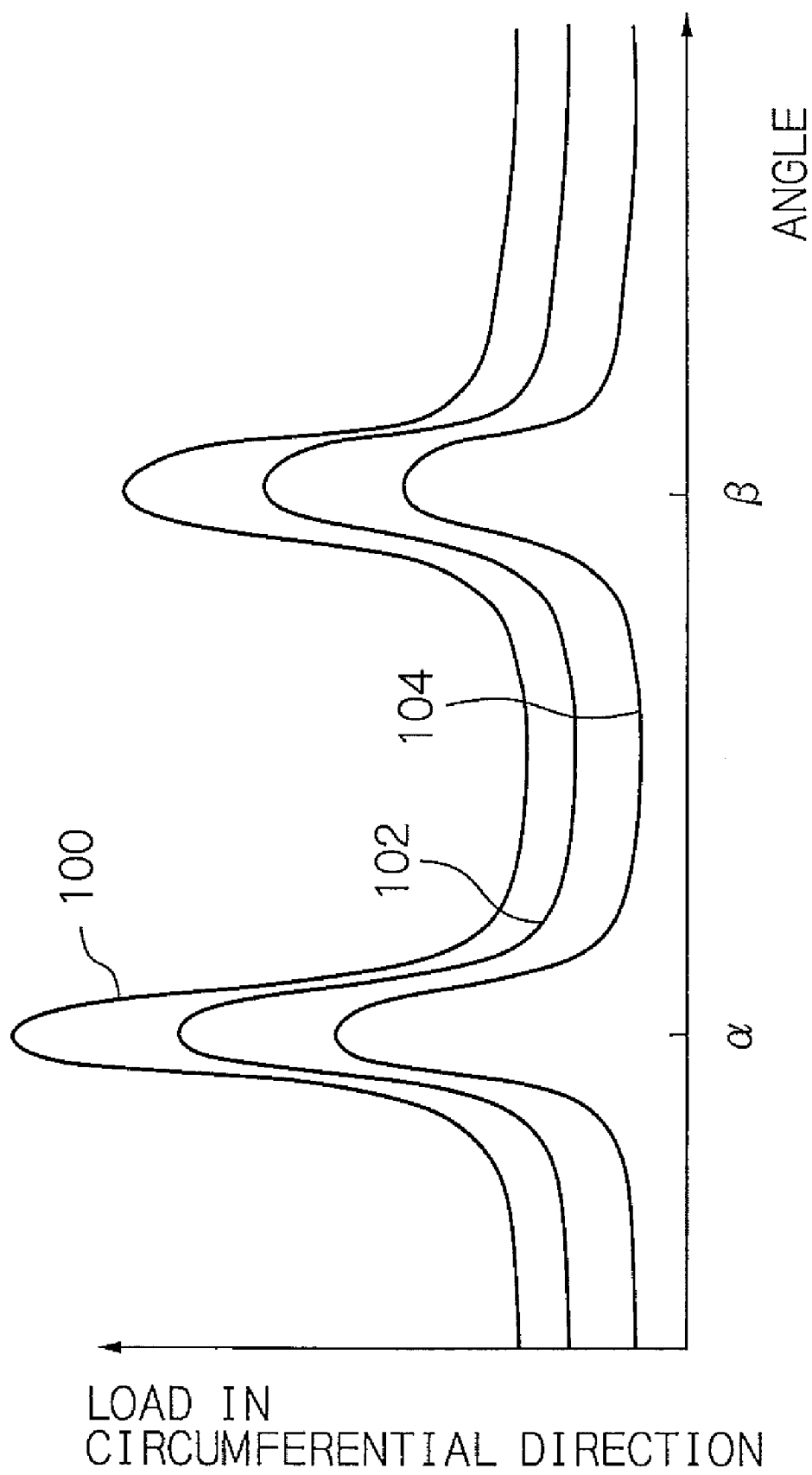
FIG. 18 is a graph showing a relationship between the posture of the robot arm and loads with respect to different speeds in the training device shown in FIG. 1A.

In addition, the load in the direction circumferential to the orbit 88 varies in response to speeds 100, 102 and 104 of three-stepwise fashion, for example a high, a medium and a low speed in order to prevent the figure from being complicated, as shown in FIG. 18. However, it is preferable to continuously vary the load rather than to vary it in a stepwise fashion according to the speed. Further, a load actually applied to the leg of the user 20 is a combination of a load in the direction vertical to the orbit drawn with the distal end of the leg of the user 20 and a load in the direction tangential to the orbit.

In this way, in the present alternative embodiment, even when the training speed has been varied due to a change in muscular force of the user 20 as the result of the training, there is no need of re-tabulating the reference table having load data stored therein, and thus an appropriate load according to the speed can be applied to the user 20.

Further, a further alternative embodiment of a training device 10 to which the invention is applied will be described. Actions and advantages similar to those of the previous embodiments will be omitted from description.

Figure 19:
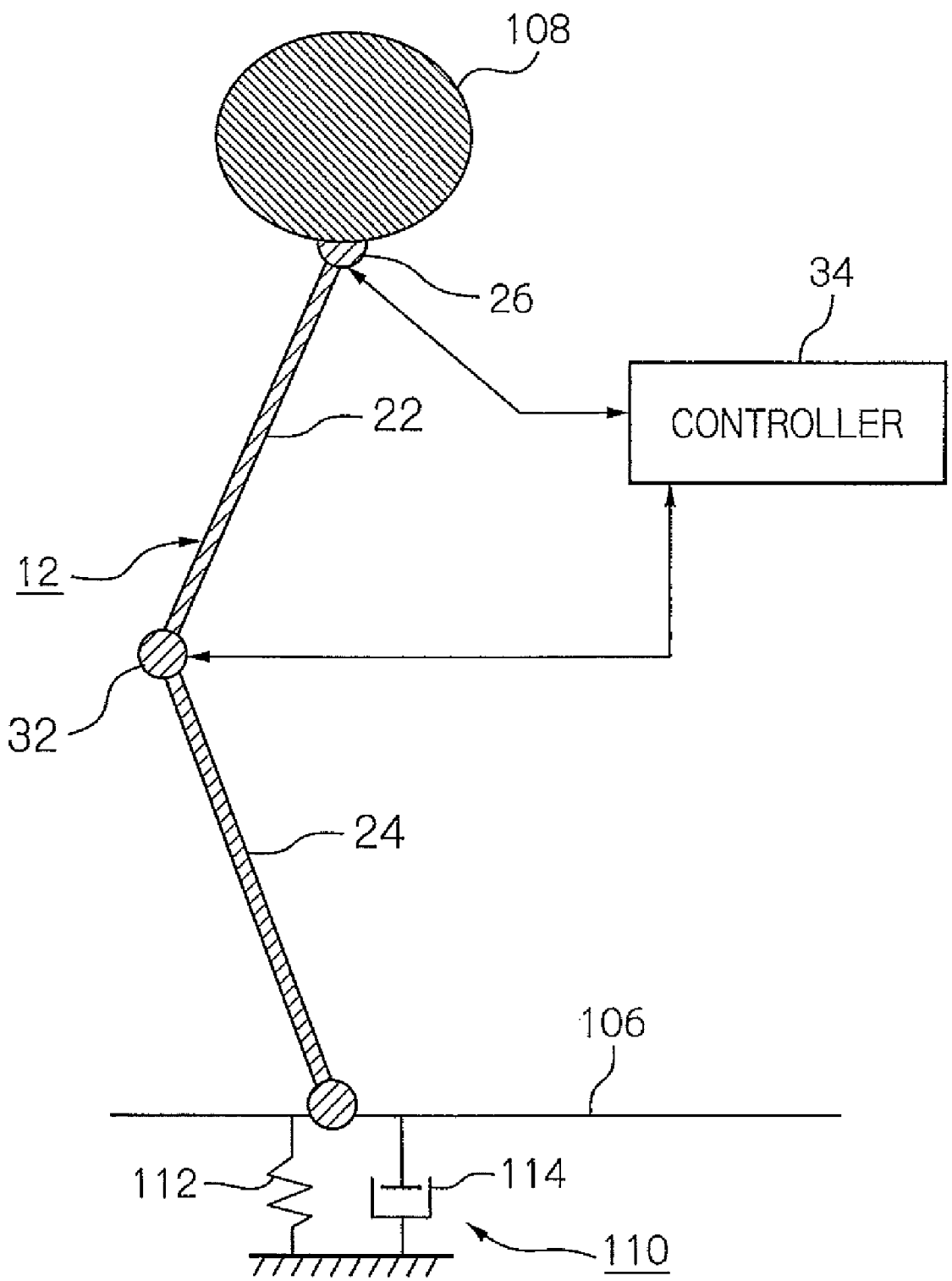
FIG. 19 shows a virtual model of the robot arm in the training device shown in FIG. 1A with a floor taken into account.

A virtual model assumed for a virtual floor in the present alternative embodiment is, as shown in FIG. 19, not directed to training with bike riding by a virtual model assumed for a virtual circular orbit 88 but to pseudo walking training in which reactive force received from a floor 106 by this virtual model is applied as a training load to the leg of the user 20.

In specific, it is set that the mass 108 corresponding to the weight of the user 20 is applied to the rear anchor of the robot arm 12, i.e. to the joint axle 26 corresponding to the hip joint of the user 20. Also, a virtual floor model 110 is assumed. The controller 34 is thus adapted to calculate reactive force that the leg of the user 20 receives from the floor 106, i.e. floor reactive force. In such a case, the floor model 110 is presumed to be of spring-damper type provided with a spring 112 and a damper 114. Further, a friction coefficient of the floor 106 is assumed to be constant. The link 14 corresponds to the thigh of the user 20 and the link 16 corresponds to his or her lower limb. The controller 34 simulates a state of the floor reactive force and the gravitational force acting on the user 20 in the virtual model and calculates the height of the hip joint of the user 20.

Here, a default value of the calculated hip joint height is set to the height of the hip joint at the time of the start training. Then, the user 20 performs training by moving his or her legs in a fashion similar to walking.

The controller 34, based on the hip joint height in the virtual model and the actual posture of the robot arm 12, calculates the interferential height between the distal end of the leg of the user 20 and the virtual floor 106. Further, the controller 34 calculates floor-reactive force in the direction substantially perpendicular to the floor 106, i.e. vertical reactive force, based on the floor model 110 of spring-damper type. Further, the reactive force in the direction substantially parallel to the floor 106 is reactive force corresponding to the inertia force of the body weight. The maximum value of the reactive force is assumed substantially equal to the maximum friction force obtained by multiplying the vertical floor reactive force by the friction coefficient of the floor 106.

In this way, the controller 34 causes the robot arm 12 to generate the resultant force of the calculated reactive force substantially perpendicular to the floor 106 and the calculated reactive force substantially parallel to the floor 106 and applies the resultant force as a training load to the leg of the user 20.

The posture of the user 20 in the training is not limited to such standing posture, but for example may be side lying posture, i.e. lying face up, or posture recumbent on a backrest. It is preferable to perform simulation on a virtual model, in which the direction of the body of the user 20 is set to the gravitational direction according to the posture of the user 20 at the time of training.

Moreover, the mass 108 corresponding to the body weight of the user 20 may not be coincided with the actual body weight of the user 20. Thus, the training device 10 can start training with a lighter load and gradually increase the load according to the state of the muscular force or joint disorder of the user 20.

As described above, in this alternative embodiment, reactive force generated by a virtual model is calculated based on the relation between the assumed virtual model and the actual posture of the robot arm 12, and then a training load corresponding to the reactive force is applied to the leg of the user 20. Thereby, the training device 10 can perform simulative walking training, while applying to the user 20 an optional load corresponding to the body weight. That allows the training device 10 to provide walking training with a load suited for the condition of the user 20, even when the user 20 is in a state of his or her muscular force having decreased due to bedridden living or in a state of having disorder in his or her joint.

Further, the user 20, when starting training, is not limited to standing posture, but may be in a state of sitting on a seat or side-lying posture, i.e. lying face up. Accordingly, the risk of falling down of the user 20 can be eliminated. Further, the floor 106 is not required to be vertical in the virtually gravitational direction but may be inclined or stepped.

Moreover, the invention is not confined to those illustrative embodiments described so far, but may be modified in various ways based on the purpose of the invention, and the modifications is not to be precluded from the scope of the invention.

The entire disclosure of Japanese patent application Nos. 2008-220613 and 2008-220629 both filed on Aug. 29, 2008, and 2008-236696 file on Sep. 16, 2008, including the specifications, claims, accompanying drawings and abstracts of the disclosure is incorporated herein by reference in its entirety.

While the present invention has been described with reference to the particular illustrative embodiments, it is not to be restricted by the embodiments. It is to be appreciated that those skilled in the art can change or modify the embodiments without departing from the scope and spirit of the present invention.

What is claimed is:

1. A training device with a muscular force measurement function, comprising:
    a robot arm adjustable according to a length of either of an upper limb and a lower limb of a trainee;
    a mounting fixture for fastening said robot arm along either of the upper limb and the lower limb;
    an angular sensor for measuring a rotational angle of a joint axle rotating integrally with said robot arm, while linking said robot arm correspondingly to a joint of the trainee; and
    a controller for controlling an axial torque of the joint axle, said controller storing, when an angular rate of the joint axle in a direction of the axial torque exceeds a predetermined value, a value of the axial torque as a maximum muscular force of either of the upper limb and the lower limb, and stopping an application of the axial torque when the angular rate exceeds the predetermined value,
    wherein said controller stores, when the a change in angle of the joint axle from a default value is out of a predetermined range, the axial torque when the angular rate of the joint axle in the direction of the axial torque has exceeded the predetermined value as the maximum muscular force of either of the upper limb and the lower limb, and stops applying the axial torque when the angular rate exceeds the predetermined value.

2. The device in accordance with claim 1, wherein said controller nullifies, when the a change in angle of the joint axle from the default value is within the predetermined range, the axial torque when the angular change of the joint axle in the direction of the axial torque has exceeded the predetermined value, and continues to apply the axial torque even when the angular rate exceeds the predetermined value.

3. A training device with muscular force measurement function, comprising:
    a robot arm adjustable according to a length of either of an upper limb and a lower limb of a trainee;
    a mounting fixture for fastening said robot arm along either of the upper limb and the lower limb;
    an angular sensor for measuring an angle of a joint axle arranged in said robot arm;
    a torque sensor for measuring an axial torque of the joint axle;
    a controller for controlling the axial torque of the joint axle; and
    a memory for storing the axial torque of the joint axle and the angle of the joint axle,
    said controller measuring, before starting at least one of muscular force measurement and muscular force training, an axial torque supporting own weight and generated in the joint axle by the own weight of either of the upper limb and the lower limb and the own weight of the robot arm, storing a relationship between the measured axial torque supporting the own weight and the measured angle of the joint axle, and correcting the axial torque of the joint axle in at least one of the muscular force measurement and muscular force training, based on the stored relationship between the axial torque supporting the own weight and the angle of the joint axle.

4. The device in accordance with claim 3, wherein the axial torque supporting the own weight is measured in a plurality of postures by varying the angle of the joint axle.

5. The device in accordance with claim 4, wherein said device sets a range of motion of the joint axle of said robot arm based on the plurality of postures.

6. The device in accordance with claim 5, further comprising a stop switch operable by the trainee for stopping the measurement of the axial torque supporting the own weight, wherein
    said device limits the range of motion of the joint axle of said robot arm within the posture in which the axial torque supporting the own weight has been measured before stoppage in association with stoppage of the measurement of the axial torque supporting the own weight.

7. A training device with muscular force measurement function, comprising:
    a robot arm adjustable according to a length of either of a upper limb and a lower limb of a trainee;
    a mounting fixture for fastening said robot arm along either of the upper limb and the lower limb;
    an angular sensor for measuring an angle of a joint axle arranged in said robot arm;

a torque sensor for measuring an axial torque of the joint axle;

a controller for controlling the axial torque of the joint axle; and a memory for storing a reference table indicating a relationship between the axial torque of the joint axle and the angle of the joint axle when a distal end of said robot arm moves to draw a predetermined orbit, said controller generating an axial torque based on the relationship stored as the reference table in said memory to thereby maintain the distal end of either of the upper limb and the lower limb to draw the orbit as well as to apply a training load for a specific group of muscles of praxis to either of the upper limb and the lower limb.

8. The device in accordance with claim 7, wherein the axial torque of the joint axle stored in the reference table includes an axial torque corresponding to a load in a direction tangential to the orbit and an axial torque corresponding to a load in the direction substantially perpendicular to the orbit, the axial torque corresponding to a load in the direction tangential to the orbit changing according to a speed in the direction tangential to the orbit.

9. The device in accordance with claim 7, wherein the orbit is substantially circular and the trainee performs bike-riding motion.

10. A training device with muscular force measurement function, comprising:

a robot arm adjustable according to a length of either of an upper limb and a lower limb of a trainee;

a mounting fixture for fastening said robot arm along either of the upper limb and the lower limb;

an angular sensor for measuring an angle of a joint axle arranged in said robot arm;

a torque sensor for measuring an axial torque of the joint axle; and a controller for controlling the axial torque of the joint axle, said controller calculating, based on a relationship between an assumed virtual model and an actual posture of said robot arm, reactive force generated in the virtual model and applying a training load substantially equivalent to the reactive force to either of the upper limb and the lower limb.

11. The device in accordance with claim 10, wherein the virtual model includes a floor model of spring-damper type, wherein the trainee performs motion of walking on a floor of the floor model.

\* \* \* \* \*